United States Patent [19]
Allibert et al.

[11] Patent Number: 5,976,789
[45] Date of Patent: Nov. 2, 1999

[54] SYSTEM OF PROBES ENABLING HLA-DR TYPING TO BE PERFORMED, AND TYPING METHOD USING SAID PROBES

[75] Inventors: Patrice André Allibert, Grezieu La Varenne; Philippe Cros, Lyons, both of France; Bernard Francois Mach, Geneva, Switzerland; Bernard Fabien Mandrand, Villeurbanne, France; Jean-Marie Tiercy, Geneva, Switzerland

[73] Assignee: Bio Merieux, Marcy L'Etoile, France

[21] Appl. No.: 08/485,133

[22] Filed: Jun. 7, 1995

Related U.S. Application Data

[63] Continuation-in-part of application No. 08/030,143, May 3, 1993, abandoned.

[30] Foreign Application Priority Data

Jul. 17, 1991 [FR] France ................................ 91 09058
Jul. 17, 1992 [WO] WIPO ..................... PCT/FR92/00702

[51] Int. Cl.$^6$ .............................. C12Q 1/68; C07H 21/02
[52] U.S. Cl. ................................................ 435/6; 536/23.1
[58] Field of Search .................... 435/6, 91.2; 536/23.1, 536/23.5, 24.31

[56] References Cited

U.S. PATENT DOCUMENTS

| | | | |
|---|---|---|---|
| 4,965,189 | 10/1990 | Owerbach | 435/6 |
| 5,310,893 | 5/1994 | Erlich | 536/24.31 |
| 5,468,613 | 11/1995 | Erlich et al. | 435/6 |
| 5,541,065 | 7/1996 | Erlich et al. | 435/6 |
| 5,567,809 | 10/1996 | Apple et al. | 536/24.3 |

FOREIGN PATENT DOCUMENTS

| | | |
|---|---|---|
| 0237362 | 9/1987 | European Pat. Off. |
| 0405913 A2 | 2/1991 | European Pat. Off. |
| 0443748 | 8/1991 | European Pat. Off. |
| 0456304 | 11/1991 | European Pat. Off. |
| 0 459 532 A2 | 12/1991 | European Pat. Off. |
| 0 472 399 A2 | 2/1992 | European Pat. Off. |
| 2 679 252 | 1/1993 | France |
| 3-164180 | 7/1991 | Japan |
| WO 88/01302 | 2/1988 | WIPO |
| 89/04875 | 6/1989 | WIPO |
| 89/11547 | 11/1989 | WIPO |
| WO 92/08117 | 5/1992 | WIPO |
| WO 92/10589 | 6/1992 | WIPO |
| WO 92/12996 | 8/1992 | WIPO |
| WO 93/09245 | 5/1993 | WIPO |

OTHER PUBLICATIONS

Scharf et al PNAS 85:3504–3508 (1989).
Wordsworth et al Immunogenetics 32:413–418 (1990).
S. J. Scharf et al., "HLA Class II Allelic Variation and Susceptibility to *Pemphigus Vulgaris*", *Proc. Natl. Acad. Sci. USA*, vol. 85, pp. 3504–3508, May 1988.
B. Mach et al., "Genotypic Typing of HLA Class II: From the Bench to the Bedside", *Human Immunology*, vol. 30, No. 4, pp. 278–284, 1991.
Gorski et al., "Polymorphism of Human Ia antigens: gene conversion between two DR β loci results in a new HLA–D/DR specificity", *Nature* 322:67–70, 1986.
Wordsworth et al., "HLA–DR typing using DNA amplification by the polynerase chain reaction and sequential hybridization to sequence–specific oligonucleotide probes", *Immunogenetics* 2:413–418, 1990.
Urdea et al., "A Comparison of Non–Radioisotopic Hybridization Assay Methods Using Fluorescent Chemiluminescent and Enzyme Labeled Synthetic Oligodeoxyribonucleotide Probes", *NucliAcid Res.* 16:4937–4956, 1988.
Dialog translated Abstract, J.P. 3–164180, 1991.

*Primary Examiner*—Eggerton A. Campbell
*Attorney, Agent, or Firm*—Oliff & Berridge, P.L.C.

[57] ABSTRACT

A set of probes for determining HLA-DR types or sub-types includes at least one of the following probes:
  TGGCAGCTTA AGTTT;
  CCTAAGAGGG AGTG;
  GCGAGTGTGG AACCT; and
  AAGACAGGCG GGC.

27 Claims, No Drawings

SYSTEM OF PROBES ENABLING HLA-DR TYPING TO BE PERFORMED, AND TYPING METHOD USING SAID PROBES

This application is a Continuation-in-Part of U.S. application Ser. No. 08/030,143, filed on May 3, 1993, now abandoned claiming foreign priority under 35 USC 119 to PCT/FR92/00702, filed on Jul. 17, 1992 and French Patent No. 91-09058, filed on Jul. 17, 1991.

The present invention relates to a method for determining an individual's class II HLA genotype, and is concerned more especially with the detection of polymorphic HLA-DR genes. This method is applicable, in particular, to HLA typing in transplantation, to medical diagnosis, to forensic medicine, and the like.

The HLA (human lymphocyte antigen) system is encoded by the major histocompatibility complex in man. It gives rise to a very substantial constraint during organ transplantations between individuals, by making a distinction between self and non-self. Furthermore, the HLA factors are involved in the predisposition to a large number of diseases. The antigens of the HLA system have hence been used in typing methods to determine the characteristics between donors and recipients during organ transplantations (F. H. BACH and J. J. VAN ROOD, N. Engl. J. Med., 295, pages 806–13 (1976)), as well as an individual's predisposition to certain diseases.

From a genetic standpoint, the HLA system is well characterized, and consists of a set of more or less polymorphic loci situated within a space of approximately 2 centimorgans (cM) on the short arm of chromosome 6. Three loci in this system (HLA-A, -B and -C) code for a class of alloantigens expressed codominantly (class I). Another region (HLA-D), which contains, in fact, several genes, codes for a second class of alloantigens expressed codominantly with a considerable degree of polymorphism (class II). Several other loci which control, in particular, components C2, C4 and factor Bf of the complement cascade also belong to the HLA system (class III). The success of organ transplants depends in large measure on HLA identity (classes I and II) between recipient and donor. Consequently, the HLA typing must be as accurate as possible. This requirement relates mainly to kidney transplantations (P. J. Morris and A. Ting (1982) Immunol. Rev 66, 103—G. Opelz (1989) Transpl. Proc. 21,609—E. L. LAGAAIJ, P. H. Hennemann, M. Ruigrok et al. (1985) New Engl. J. Med. 321,701) and bone marrow grafts (P. G. Beatty, R. A. Clift, E. M. Mickelson et al. (1985) New Engl. J. Med 313,765—J. M. Hows and B. A. Bradley (1990) British J. Hematol. 76,1). In the context of bone marrow grafting, perfect identity in respect of the class II HLA antigens represents a decisive factor for the success of the grafting, that is to say to avoid rejection of the graft or development of a graft-versus-host disease (P. G. Beatty, J. Hansen, G. M. Longton et al. (1991) Transplantation 51, 443—R. C. Ash, J. T. Casper, C. R. Chitambar et al. (1990) New Engl. J. Med. 322, 485—C. Anasetti, D. Amos, P. G. Beatty et al. (1989) New Engi. J. Med. 320,197).

The polymorphism of the expression products of the genes of the HLA-D region is usually defined by serological techniques based on analysis with alloantisera of the HLA gene products expressed at the surface of the cells (J. J. Van Rood and A. Van Leeuwen (1963) J. Clin. Invest. 42,1382—J. J. Van Rood, A. Van Leeuwen, J. J. Koning, A. B. Van Oud Ablas (1975) Tissue Antigens 5, 73). The accuracy and reproducibility depend on the batches of sera available. However, even under the best conditions, a very large number of existing alleles are not detectable by these serological techniques. The limitations of serological analysis result chiefly from the absence of monospecific alloantisera, from an incomplete discrimination with cross-reactivities between very closely related specificities, for example DR3 and DRw13, or alternatively from an altered expression of the class II HLA molecules at the surface of the cells, for example of leukemic cells.

Employing molecular biology, a much larger number of HLA genes are now known to exist than had previously been supposed, and, most especially, many more different alleles. This diversity is now characterized in terms of the DNA sequences of the different genes and alleles. According to the latest report of the HLA Nomenclature Committee (see The WHO Nomenclature Committee for factors of the HLA system (1990) Immunogenetics 31, 131—and —J. G. Bodmer, S. G. E. Marsh, E. D. Albert, W. F. Bodmer, B. Dupont, H. A. Erlich, B. Mach, W. R. Mayr, P. Parham, T. Sasazuki, G. M. T. Schreuder, J. L. Strominger, A. Svejgaard and P. I. Terasaki (1991) Tissue Antigens 37, 97), the class II HLA polymorphism is distributed as follows: DRB1 locus: 47 alleles, DRB3 locus; 4 alleles, DRB4 locus: 1 allele, DRB5 locus: 4 alleles, DQB1 locus: 17 alleles, DQA1 locus: 13 alleles, DPB1 locus: 21 alleles, DPA1 locus: 4 alleles.

Many of these alleles elude serological analysis and are identifiable only in terms of the DNA. The limitations of serological typing may be illustrated by the DR4 serological specificity, now subdivided into 11 subtypes (DRB1*0401–0411) (see J. G. Bodmer, S. G. E. Marsh, E. D. Albert, W. F. Bodmer, B. Dupont, H. A. Erlich, B. Mach, W. R. Mayr, P. Parham, T. Sasazuki, G. M. T. Schreuder, J. L. Strominger, A. Svejgaard and P. I. Terasaki (1991) Tissue Antigens 37, 97) which are identifiable only in terms of the DNA sequence.

Similarly, the DRw6 specificity, which may be subdivided into DRw13 and DRw14 with a few alloantisera, actually contains 10 allelic sequences (DRB1*1301–1305 and DRB1*1401–1405) (see the publication of Bodmer J. G. cited above) which, here too, can be discriminated only by genotypic analysis in terms of the DNA sequence.

Genotypic analysis is a novel approach enabling the-diversity of the class II HLA system to be analyzed directly in terms of the genes. Genotypic analysis is based on the principle of molecular hybridization, and the first approach which was proposed is the so-called "RFLP" technique, which consists in fragmenting the DNA by the use of restriction enzymes and analyzing the size of the specific DNA fragments generated by these enzymes (see C. T. Wake, E. O. Long and B. Mach (1982) Nature 300, 372—J. Bihme, M. Andersson, G. Andersson, E. Miller, P. A. Peterson and L. Rask (1985) J. Immunol. 135, 2149—J. L. Bidwell, E. A. Bidwell, D. A. Savage, D. Middleton, P. T. Klouda and B. A. Bradley (1988) Transplantation 45, 640).

RFLP analysis enables only some of the allelic differences which are undetectable by serology to be recognized, and this technique still has limitations. In effect, an allele carrying a different sequence is identifiable only if the different nucleotide is in the recognition site of the restriction enzyme used in the analysis, and hence a large number of class II HLA alleles will not be recognized by this analysis. Furthermore, RFLP analysis rarely detects a modification in a coding sequence, and does not provide information about the exact nature of the modification. Lastly, this technique is lengthy and tedious, since it involves the use of relatively large quantities of nucleic acid which have to be digested with several restriction enzymes, electrophoretic runs and transfers onto filters.

To illustrate the limitations of the RFLP technique, it may be mentioned that the subtypes of the DR1, DR4, DRw8, DRw11 or DRw13 specificities are not detectable by RFLP.

A novel technique of genotypic analysis of class II HLA has been proposed, which is the method referred to as "typing with oligonucleotides". As a result of the knowledge of the DNA sequences of the class II HLA genes, and especially of the DRβ genes which are by far the most polymorphic, oligonucleotides which are specific for a given place in the sequence of the gene may be used as tracers for analysis of the polymorphism by hybridization. These oligonucleotides are chosen so as to be the most informative possible, and to permit identification of the different alleles on the basis of their differences in sequence. In practice, any difference in sequence, even a single nucleotide, may be detected.

The technique of typing with oligonucleotides may be applied equally well to DNA, as described in the publication of Angelini et al., Proc. Natl. Acad. Sci. USA Vol. 83, pages 4489–4493 (1986), and to RNA (see C. Ucla, J. J. Van Rood, J. Gorski and B. Mach (1987) J. Clin. Invest. 80, 1155).

This novel approach is based on the principle of molecular hybridization using the characteristic properties of nucleic acids, which are the possibilities of interacting with a complementary sequence via hydrogen bonds and of thereby forming a stable hybrid, according to the known laws of pairing, that is to say A-T, G-C for DNA and A-U, G-C for RNA. Thus, synthetic oligonucleotides corresponding to DNA or RNA sequences of known alleles may be used as probes to identify, in a sample, a nucleic acid sequence referred to as the target, containing a sequence complementary to that of the probe. Labelling of the hybrid formed between the target and the probe permits detection and quantification of the target in the sample. This labelling is accomplished with any known label, such as an enzymatic, chemical or radioactive label. On the basis of these principles, the first application of typing with an oligonucleotide for class II HLA was presented by Angelini et al. in the publication cited above, with the use of the so-called "SOUTHERN" technique according to which the target DNA is deposited on a nylon membrane and detection is performed using a labelled oligonucleotide probe. The technique was then applied to the detection of class II HLA alleles which are not identifiable by routine serology (see J. M. Tiercy, J. Gorski, M. Jeannet and B. Mach (1988) Proc. Natl. Acad. Sci. USA 85, 198—J. M. Tiercy, J. Gorski, H. Bétuel, A. C. Freidel, L. GebÅhrer, M. Jeannet and B. Mach (1989) Human Immunol. 24, 1). Another direct application to class II HLA typing is that described in Patent Application PCT WO 89/11547, using the so-called "Dot Blot" technique. A modification of these techniques is represented by the so-called "Reverse Dot Blot" method, which consists in binding a nucleotide probe to a membrane of paper, nitrocellulose or a mixture of the two, and performing the detection of a hybridization with a labelled target. This technique has been applied to HLA-DQA typing and to the detection of mutations of Mediterranean β-thalassemia (R. K. Saiki et al., Proc. Natl. Acad. Sci. USA, Vol 86, pages 6230–6234 (1989)).

As described above and explained in the publications and the patent application cited above, cell typing necessitates the detection of point mutations in the genome and involves the development of probes which are sufficiently sensitive to detect and differentiate sequences which are homologous except in respect of a single nucleotide, and it has been found to be necessary to use short probes, generally of less than 30 nucleotides, which endow the test with great specificity while retaining good sensitivity. The use of short oligonucleotides makes it possible to have available a wide spectrum of selectivity.

In the case where a test comprising the binding of a probe to a solid support is used, there remains the problem associated with immobilization of a short probe, of less than 30 nucleotides, to such a solid support. R. K. SAIKI et al., in the publication cited above, have proposed a method which consists in coupling a poly(dT) tail of 400 bases to the 3' end of a probe comprising between 15 and 20 bases, and immobilizing the probe via this tail on a nylon filter by exposure to ultraviolet rays so as to couple covalently the thymine bases to the primary amines present in the nylon.

However, this method is not entirely satisfactory, since it presents problems of specificity. In effect, the thymine bases of the probe can also react under UV radiation with the support, thereby involving a decrease in the efficiency of hybridization.

Moreover, for reasons of commercialization, it is desirable to develop a typing method which has great specificity and good sensitivity but which, furthermore, is simple to carry out, rapid to implement, inexpensive, capable of automation and useable for individual typing.

A new method has now been found for determining an individual's HLA-DR genotype, which overcomes the drawbacks described above while enabling sequences which are homologous except in respect of a single nucleotide to be detected and differentiated.

The method of the invention is carried out using a set of nucleotide probes chosen so as to permit typing with a minimum number of probes. This set of probes has, in particular, the advantage of making it possible to work at a single temperature, in particular at 37° C. (although it is possible to work at another temperature, as will be seen in the experimental part below). Such a set of probes also forms part of the invention.

The set of probes of the invention, which will be defined below, may be used in the form of detection probes (labeled with a standard tracer agent) in techniques of the Southern type, or, preferably, in the form of capture probes (sandwich or reverse dot blot technique) immobilized on a solid support, either by passive binding (adsorption) directly or via a ligand such as a hydrophobic ligand (see, for example, European Patent Application No. 0,405,913), or by the establishment of at least one covalent bond which can be made, here too, directly or via a ligand capable of binding covalently to the support (see, for example, Patent Application PCT No. WO 88/01,302). The immobilization of the probes may be carried out either using known methods, or using other methods which will be described below.

The probes of the invention (nucleotide probes) will be described mainly in the form of nucleotide sequences. It is obvious to a person skilled in the art that, even in the case of probes intended for detecting point mutations, at a given temperature, it is possible to envisage the use of probes of variable length (number of nucleotides), to a certain extent, in particular by means of the use of solutions and buffers that are more or less favorable to the stability of the hybridization complexes. The probes of the invention are hence defined by a sequence which may generally be considered to be maximal (especially if it is desired to work at relatively low temperature, for example at 37° C.), with, in addition, an indication of the minimum sequence which will still be useable at said temperature, and which will be sensitive to even a point mutation.

It is obvious to an expert that each particular nucleotide probe has its corresponding complementary probe, which is naturally capable of playing the same part as a capture or detection probe. The invention hence extends to such probes having a sequence complementary to those which will be described below.

It is also obvious to an expert that it is generally possible to replace, in a set of probes, one of the probes that recognizes some particular specificity X by a system of two probes, one of them recognizing specificities X and Y and the other, specificities X and Z, in which case positive responses both with the XY probe and with the XZ probe enable the presence of the specificity X to be inferred. The invention hence extends to a system of probes, as will be defined below, in which one or more probes are replaced by such an equivalent system of two probes or several probes. Naturally, such a combination system may be applied to a number of specificities greater than 2.

The subject of the invention is hence a set of probes enabling the HLA-DRβ types and/or the associated subtypes to be determined according to the techniques of typing with oligonucleotides, said set of probes comprising at least the following nucleotide probes (the underlined portion corresponding to the optimum sequence):

| | | | |
|---|---|---|---|
| (G)CTGGAAAGATGCA(T) | (SEQ ID NO:1) | CAGCAGGATAAGTATG(A) | (SEQ ID NO:2) |
| (G)TGGACAACTACT(G) | (SEQ ID NO:3) | GATACTTCTATCACC(AA) | (SEQ ID NO:4) |
| (G)CCTGATGAGGAGTA(C) | (SEQ ID NO:5) | (T)GGCAGGGTAAGTATAAG | (SEQ ID NO:6) |
| (G)GGCCCTGGTGGA(CA) | (SEQ ID NO:7) | (T)GCGGTATCTGCACA | (SEQ ID NO:8) |
| GGAGGAGGTTAAG(TT) | (SEQ ID NO:9) | (C)TGGAAGACGAGC(G) | (SEQ ID NO:10) |
| (T)GGAAGACAAGCG(G) | (SEQ ID NO:11) | (T)GCGGAGCACTGG(A) | (SEQ ID NO:12) |
| (A)CCAGIAGGAGAACGT(G) | (SEQ ID NO:13) | (A)CCAGGAGGAGAACGT(G) | (SEQ ID NO:14) |
| (A)CTCTACGGGTGAGT(G) | (SEQ ID NO:15) | (G)ACACCTATTGCAGA(C) | (SEQ ID NO:16) | or probes containing sequences of at least five nucleotides, and especially of at least eight nucleotides, said sequences being chosen from within the optimum sequences;

it being possible for said probes to be in labeled form, or coupled covalently to a ligand facilitating binding to a solid support, or bound (directly or indirectly) to a solid support.

The probe 34a can, in particular, be used in the form:

AACCAGIAGGAGAACGT(SEQ ID NO: 17)

The invention relates, in particular, to a set of probes, as defined below, which comprises, in addition, the following probes (the underlined portion corresponding to the optimum sequence): sequences 42 and 42a, and/or the following ones: 52, 37, 55.

to be generally associated to DRB1*02 type), can be replaced by the following probe (SEQ ID NO: 79)

CCTAAGAGGGAGTG, which identifies directly the DRB1*02 type.

The underlined portions of the given sequences correspond to the optimal sequence.

The set of probes of this invention may also contain at least one probe chosen among those corresponding to the following optimal (underlined) sequences:

GCGAGTGTGGAACCT (SEQ ID NO: 80);

AAGACAGGCGGGC (SEQ ID NO: 81).

A probe corresponding to SEQ ID NO:80 identifies the DRB4*01 type, while SEQ ID NO: 81 serves to identify the DRB1*1305 type.

The invention also relates to a set of probes for HLA-DR typing which includes at least one probe chosen among those corresponding to the following sequences : SEQ ID NOs: 2, 3, 6, 9, 13–16, 17–19 and 21 and optionally SEQ ID NOs: 78–81, it being understood that each probe has a minimum sequence of at least 5 (or at least 8) contiguous nucleolides of the non-parenthesized portion of, respectively, one of said following sequences, and that each probe has a maximum sequence of, respectively, one of said following sequences, including the parenthesized portions.

The Invention further relates to a set of probes for HLA-DR typing which includes at least one probe chosen among those corresponding to the following sequences : SEQ ID NOs: 2, 3, 6, 9, 12–16, 17–21 and optionally SEQ ID NOs: 78–81, it being understood that each probe has a minimum sequence of at least 8 contiguous nucleotides of the non-parenthesized portion of, respectively, one of said following sequences, and that each probe has a maximum sequence of, respectively, one of said following sequences, including the parenthesized portions.

| | | | |
|---|---|---|---|
| (G)AGGAGGACTTGCGC(T) | (SEQ ID NO:18) | (T)ACGGGGCTGTGGA(G) | (SEQ ID NO:19) |
| (G)GAGCTGCGTAAG(T) | (SEQ ID NO:20) | TTCCTGGAGAGACAC | (SEQ ID NO:21) |
| (G)GGAGAGATACTTC(C) | (SEQ ID NO:22) | | |

Examples of HLA DR types which can be identified with the probes of this invention are given in Example 4 and Table 6 hereafter. Probe 34a can replace probe 28 (or probe 33) of Table 4 hereafter. A probe corresponding to SEQ ID NO: 1 which identifies DRB1*01 (see Table 6), can be replaced by the following probe (SEQ ID NO: 78):

TGGCAGCTTAAGTTT.

A probe corresponding to SEQ ID NO; 2, which identifies (see probe 5, Table 6) certain DRB5 types (which are known The subject matter of the invention is also a method for determining an individual's HLA-DRβ typing according to the standard techniques of typing with oligonucleotides, wherein at least a portion of the probes of the set of probes as defined above is used as capture or detection probes, either sequentially or simultaneously.

In an automated method, a set of probes allowing the identification of every known HLA-DR type or subtype of interest may be used. In other cases, it is obviously possible to use them one after the other and to stop the method when the information gathered suffices for determining the typing.

The method of the invention hence essentially comprises the steps consisting in:

bringing samples of target nucleic acids containing the polymorphic regions of an individual's HLA-DR gene into contact according to a chosen particular technique with at least a portion of the set of probes as defined above, incubating according to known methods under predetermined conditions such that hybridization with each probe takes place only if the target contains a sequence fully complementary to that of said probe, and determining, according to standard detection techniques, the hybridization or lack of hybridization with each of the probes used.

The information gathered is then used to determine the typing in accordance with a pre-established typing plan, taking account of the probes used and the knowledge of the HLA-DR types and/or associated subtypes listed. This work is simplified by the use of a typing plan, that is to say, in practice, a table giving the types and/or subtypes directly in accordance with the positive responses (hybridization(s)) observed. For the set of probes of the present invention, such a table is given below in the experimental part (see Table 6).

The invention relates especially to a method as defined above in which said probes are used as capture probes, it being possible for this method to be distinguished by the fact that it comprises the steps consisting in:

a) immobilizing each capture probe on a solid support, b) bringing each immobilized capture probe into contact with a liquid medium containing at least one target nucleic acid fragment, under predetermined conditions permitting hybridization if the sequence complementary to that of the probe is present in the target, and c) detecting the presence of any hybrids which may be formed.

Naturally, the probes of the invention enable both RNA and DNA target fragments to be detected. Moreover, it is obviously possible to use as a detection probe, apart from the above probes, all suitable probes, in particular one of the probes described below in Example 5.

When the capture probe is very short, that is to say smaller than 20 nucleotides and especially smaller than 17 nucleotides, it becomes necessary to employ means that enable the binding of the probe to a solid support to be improved. The binding of the probe to the support is then performed in the form of a derivative resulting from covalent coupling of the probe with a ligand that facilitates binding to the solid support. The ligand, which can comprise a hydrophobic portion, is, in particular, a ligand comprising at least one polar functional group, for example an amino group. The functional group can serve to bind the probe to the solid support by establishment of a covalent bond. When the polar functional group does not react with the support, it improves the binding by adsorption on the support, even if the support is hydrophobic.

The ligand is, for example, chosen from proteins and compounds as represented, respectively, by the formulae I and II below:

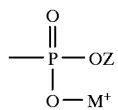

in which:
Z represents a linear or branched alkyl or alkenyl radical having 2 to 12 carbon atoms, unsubstituted or substituted with one or more groups chosen from hydroxyl and/or amino groups, and $M^+$ represents, in particular, an alkali metal or ammonium ion.

This ligand is preferably coupled to the 5' end of the nucleotide sequence of the capture probe;

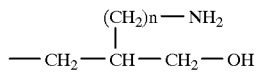

in which n is an integer which can vary from 1 to 4, and preferably n=1 or 4.

This ligand is preferably coupled to the 3' end of the nucleotide sequence of the capture probe.

When the ligand is a protein, an albumin, for example, is chosen, preferably bovine serum albumin, which may be coupled to the 5' or 3' end of the nucleotide sequence of the capture probe.

The support of the present invention can be any support enabling a nucleotide sequence or a derivative according to the invention to be immobilized, either by passive adsorption or by covalent bonding. The supports may be made of any material customarily used, such as nitrocellulose, nylon, paper, or preferably of a hydrophobic material such as a styrene polymer or a copolymer based on styrene comprising at least 10% by weight of styrene units.

The solid support according to the invention can be, without limitation, in the form of a microtitration plate, a sheet, a tube, a cone, wells, or the like.

According to the method of the present invention, a sample containing a nucleic acid is obtained from an individual whose HLA-DR genotype is to be determined. Any type of tissue containing HLA-DR nucleic acid may be used in the context of the present invention. It is thus possible to use nucleic acid (DNA or RNA) fragments obtained after cleavage of the nucleic acid present in the individual's sample by chemical, enzymatic or the like means.

However, the incorporation of a prior step of amplification of the target DNA or RNA can facilitate the method for typing with an oligonucleotide of the present invention. The principle of the analysis of HLA polymorphism by hybridization of sequence-specific oligonucleotides remains the same, but a selective amplification step permits an enrichment in sequences of the target, thereby simplifying the technique (R. K. Saiki, T. L. Bugawan, G. T. Horn, K. B. Mullis and H. A. Erlich (1986) Nature 324, 163—J. M. Tiercy, M. Jeannet and B. Mach (1990) Eur. J. Immunol. 20, 237).

The amplification may be obtained either from DNA or from RNA. It is obvious to a person skilled in the art that the amplification of the sequences of the HLA-DR target in a sample may be accomplished by any known method which enables sufficient amplification to be obtained for it to be possible to detect the sequence of the target by hybridization of a nucleic acid to a probe.

In general, the nucleic acid in the sample will be DNA, most often genomic DNA. However, the present invention may also be carried out with other nucleic acids such as messenger RNA or cloned DNA, and the nucleic acid in the individual's sample may be in single-stranded or double-stranded form. Naturally, when the nucleic acid is in double-stranded form, it is necessary to perform a denaturation step to obtain a single-stranded nucleic acid.

The probes used in the present invention are sequence-specific oligonucleotides (SSO) which, under suitable conditions, can bind specifically to their complementary sequences. If a particular probe can be used to identify an allele uniquely, the probe is then referred to as ASO, that is to say allele-specific oligonucleotide. It is possible for a single probe to be incapable of identifying on its own a DRβ specific allele on account of the differing nature between various DRβ alleles.

According to the method of the invention, the identity of an allele is deduced from a model of binding of a set of probes, each individual probe of the set being specific for different portions of the HLA-DR genes. As a result of the choice of a multiplicity of probes corresponding to the DNA sequences of the known alleles, the specificity of the method for typing with oligonucleotides of the present invention enables all the alleles of the DRB1, DRB3 and DRB5 loci to be identified. Naturally, the method of the present invention could be used to identify the alleles of other extremely polymorphic loci such as DQB1 and DPB1. Since the allelic differences are essentially localized in the exon coding for the first domain of the HLA molecules (aa 5–94), the probes are chosen to be complementary to specific sequences localized in this region. In the event of new alleles being discovered, the latter are immediately listed in a register of class II HLA sequences, which enables the collection of informative tracers to be updated, and the methodology hence to be adapted to the detection of any new allele.

To rationalize the complete class II HLA typing, it has been proposed to introduce, in the first place, a first step of generic DR typing, which can recognize the main HLA-DR specificities, that is to say HLA-DR1-DRw18, with a limited number of probes. This step is sufficient for a large number of clinical applications (see B. Mach and J. M. Tiercy (1991) Human Immunol. 30, 278).

On the basis of the results of this first step, it is possible to choose the specific probes needed to produce, in a second stage, a DRβ micropolymorphism, to detect the DQB1 polymorphism and, if necessary, to characterize the DPB1 alleles.

The analysis of the HLA-DR1-DRw18 specificities by the technique of typing with oligonucleotides may be applied in histocompatibility laboratories for routine DR typing, as a replacement for DR serology, in particular to perform the DR typing of patients on a waiting list for a kidney transplant or the typing of potential kidney donors, the DR typing of leukemia patients for whom a bone marrow graft is envisaged, as well as of members of their family or unrelated potential donors, large-scale DR typing for the compilation of registers of voluntary marrow donors, to determine associations between diseases and the HLA system, for example in the case of insulin-dependent diabetes, for applications in predictive medicine or alternatively for tests for paternity and other forensic identifications.

A few definitions of terms used in the present application are given below:

"genotype" refers to the set of genotypic characteristics of an individual, as opposed to the "phenotype" which comprises the features of an individual as emerge from the analysis of the expression products of the gene, and in particular of the proteins.

"alleles" are the different alternative forms of the same gene which exhibit differences in the nucleic acid sequence. These differences are manifested in the DNA, the RNA and the proteins.

"polymorphism" characterizes the diversity introduced into a population by the existence of different alleles for the same gene.

"oligonucleotide" as used here denotes primers, probes, nucleic acid fragments which are to be detected, and the like. The oligonucleotides may be prepared by any known suitable method.

"nucleotide probe" represents a natural DNA or RNA fragment, or a natural or synthetic oligonucleotide, or a synthetic DNA or RNA fragment, unmodified or comprising one or more modified bases such as inosine (designated by the letter I), 5-methyldeoxycytidine, 5-(dimethylamino)-deoxyuridine, deoxyuridine, 2,6-diaminopurine, 5-bromodeoxyuridine or any other modified base permitting hybridization.

Moreover, in the present application, when the sequences of the capture probes are underlined, this represents the optimal sequence for the typing according to the invention. Naturally, these optimal sequences may be elongated at the 3' and/or 5' end by at least one base. In this case, some bases which can optionally be added have been shown in brackets, as may be seen, for example, on reading the description below. Lastly, it is possible for a person skilled in the art to modify the length of the sequences used in accordance with the working conditions (such as: hybridization and washing temperatures, the nature of the hybridization and/or washing buffer) and the typing plan.

A better understanding of the invention will be gained on reading the detailed description which follows, prepared with reference to non-limiting examples illustrating preferred embodiments of the method of the invention.

EXAMPLE 1

The ligands used in the present invention, and given here by way of example, can be commercially available compounds, as in Table 1 below:

TABLE 1

| ligand | Formula | Supplier | ref |
|---|---|---|---|
| a | $CF_3-C(=O)-NH-(CH_2)_6-OP(OCH_3)(N(isoPr)_2)$ | Applied Biosystems | 400808 |

TABLE 1-continued

| ligand | Formula | Supplier | ref |
|---|---|---|---|
| b | MMTr—NH—(CH$_2$)$_{12}$—O—P(O—(CH$_2$)$_2$—CN)(N(isoPr)$_2$) | Clontech Lab Inc | 5206-1 |
| c | MMTr—NH—(CH$_2$)$_3$—O—P(O—(CH$_2$)$_2$—CN)(N(isoPr)$_2$) | GlenResearch | 10-1903 |
| d | Fmoc—NH—CH$_2$—CH(OP(O—(CH$_2$)$_2$—CN)(N(isoPr)$_2$))—CH$_2$—O—DMTr | Clontech Lab Inc | 5203-3 |
| e | CPG—LCAA—O—CH$_2$—CH(CH$_2$—NH—Fmoc)—CH$_2$—ODMTr | Clontech Lab Inc | 5221-1 |
| f | CPG—LCAA—O—CH$_2$—CH((CH$_2$)$_4$—NH—Fmoc)—CH$_2$—ODMTr | Clontech Lab Inc | 5222-1 |

MMTr = monomethoxytrityl
DMTr = dimethoxytrityl
Fmoc = 9-fluorenylmethoxycarbonyl
CPG = controlled-pore glass beads
LCAA = long-chain alkylamine (spacer arm)

The coupling of a phosphoramidite ligand to an oligonucleotide is performed according to the following general protocol:

An oligonucleotide is synthesized on an APPLIED BIOSYSTEMS company automatic apparatus 381 A using phosphoramidite chemistry according to the constructor's protocol. The phosphoramidite ligand dissolved in anhydrous acetonitrile at a concentration of 0.2M is placed at position X of the synthesizer, and addition of the ligand takes place at the 5' end of the oligonucleotide according to the standard protocol of automatic synthesis when the synthesis of the oligonucleotide is complete.

In the case where the ligand carries a dimethoxytrityl protective group, such as for the compound d, it is necessary to perform an additional step of deprotection of the trityl group with trichloroacetic acid at the end of the synthesis.

After deprotection overnight at 55° C. in 33% NH$_4$OH followed by precipitation in ethanol at −20° C., the oligonucleotide is dried under vacuum and taken up in 1 ml of H$_2$O.

For the compounds bearing references b and c, an additional step of cleavage of the monomethoxytrityl group is performed according to the protocol of the manufacturer (CLONTECH and GLEN RESEARCH, respectively) after deprotection.

In the case of the compounds bearing the references e and f, the automatic synthesis begins with the silica grafted with the ligand according to the standard protocol. The coupling of ligand and oligonucleotide takes place via the 3' end of the latter.

In all cases, the oligonucleotides modified at their 5' or 3' ends are purified by reversed-phase high pressure liquid chromatography (HPLC) on a Brownlee RP18 column (10 mm×25 cm).
Conditions: flow rate 4.6 ml/min gradient 10% to 35% of buffer B in the course of 30 min. 35% to 100% of buffer B in the course of 3 min.

The characteristics of the buffers A and B are as follows:
Buffer A: 0.1 molar triethylammonium acetate (TEAA) pH 7.00
Buffer B: 50% Buffer A+50% CH$_3$CN.

EXAMPLE 2

Coupling of an oligonucleotide to bovine serum albumin (BSA).

An oligonucleotide carrying the amino link 2 arm, bearing reference a in Table 1, is synthesized as described in Example 1: 3×10$^{-8}$ mol of oligonucleotide is dried under vacuum and taken up in 25 μl of 0.1M sodium borate buffer, pH 9.3. 500 μl of a solution containing 30 mg/ml of DITC (1,4-phenylene diisothiocyanate, Fluka 78480) in DMF are added. The mixture is stirred for 1.5 h at room temperature before adding 3 ml of H$_2$O. After extraction of the solution with butanol (3×3 ml), the remaining aqueous phase (500 μl) is dried under vacuum and then taken up with 1×10$^{-7}$ mol (6.6 mg) of BSA (Pierce 30444) in 400 μl of borate buffer (0.1 molar pH 9.3). After being stirred overnight at room temperature, the conjugate is purified by ion exchange using HPLC on an AX300 column (BROWNLEE 4.6×100 mm) with an NaCl gradient (Table 1). The conjugate peak is dialyzed against water (2×1 liter), concentrated under vacuum, taken up with 1 ml of H$_2$O and stored at −20° C.
Chromatographic conditions:
gradient of: 10% B' to 56% B' in the course of 25 min.
56% B' to 100% B' in the course of 2 min.
The characteristics of the buffers A' and B' are as follows:
A'=20 mM sodium phosphate, pH 7.00; 20% CH$_3$CN
B'=Buffer A'+1M NaCl or 2M NaCl.

EXAMPLE 3

Table 2 shows the alignments of amino acids for the different alleles of the DRBeta gene with the aim of defining the positions of the mutated amino acids relative to the chosen consensus sequence (referred to as "DR CONS"). These mutations correspond to non-silent mutations in the DNA, that is to say mutations which will induce a change in amino acid. The amino acids are, in effect, known to be encoded in the DNA by triplets of bases. A mutation at the third position will generally not lead to a change in amino acid. In contrast, a change in the second base will quite often induce a change in amino acid. Lastly, a mutation at the first base will always lead to a modification of the amino acid.

In the case of the typing of the different alleles, mutations on the DNA corresponding to non-silent mutations are hence used most often. However, it is possible to detect a mutation of the silent type, for example with the aim of differentiating 2 very closely related alleles.

Table 3 shows the alignments of the nucleotides of the DRBeta gene for all the alleles known and published in the literature to date, relative to the same consensus sequence as in Table 2.

The nomenclature used to designate the different alleles is that proposed at the Fifth Conference on Histocompatibility (Leiden, Holland, 1991). The designations in brackets in Table 2 represent the previous nomenclature.

TABLE 2

```
                              10         20         30         40         50         60         70         80         90
                               *          *          *          *          *          *          *          *          *
DR CONS           PRFLEQxKSECHFFNGTERVRFLDRYFYNQEEYVRFDSDVGEYRAVTELGRPDAEYWNSQKDLLEQRRAAVDTYCRHNYGVGESFTVQRR    (SEQ ID NO:23)
DRB1*0101 (Dw1)   ----W-L-F----------L-E-CI-----S-----------------------------------------------------------
DRB1*0102 (Dw20)  ----W-L-F----------L-E-CI-----S-----------------------------------------------------AV-----
DRB1*0103 (DwBON) ----W-L-F----------L-E-CI-----S-----------------I-DE----------------------------------------
DRB1*1501 (Dw2)   ----W-P-R---------------------S-----F-------------I-A---------------------------------------
DRB1*1502 (Dw12)  ----W-P-R---------------------S-----F-------------I-A-------------V-------------------------
DRB1*1601 (DW21)  ----W-P-R---------------------S---------------------F-D-------------------------------------
DRB1*1602 (Dw22)  ----W-P-R---------------------S---------------------L-D-------------------------------------
DRB1*0301 (DRw17) ----YST------------Y------N---F-----------------------------K-GR--N---V---------------------
DRB1*0302 (DRw18) ----YST------------E--H---N---------------------------------K-GR--N-------------------------
DRB1*0401 (Dw4)   ------V-H----------H--------------------------------------K---------------------------------
DRB1*0402 (Dw10)  ------V-H----------H----------------------------------------I-DE----------------------------
DRB1*0403 (Dw13TAS)------V-H----------H---------------------------------------E---------V---------------------
DRB1*0404 (Dw14)  ------V-H----------H----------------------------------------E---------V---------------------
DRB1*0405 (Dw15)  ------V-H----------H----------------------------------------------------V-------------------
DRB1*0406 (KT2)   ------V-H----------H-S----------------------------S---------E---------V---------------------
DRB1*0407 (Dw13JHA)------V-H----------H----------------------------------------E---------V---------------------
DRB1*0408         ------V-H----------H----------------------------------------K--------------------------------
DRB1*0409         ------V-H----------H----------------------------S---------------------V----------------------
DRB1*0410         --------------------H---------------------------S---------------------V----------------------
DRB1*0411         --------------------H---------------------------S-------E-----------V-----------------------
DRB1*0701 (Dw17)  ----W-G-YK---------Q-E-L------F--------------------V-S------I-D-GQ----V---------------------
```

TABLE 2-continued

```
                                 10         20         30         40         50         60         70         80         90
                                  *          *          *          *          *          *          *          *          *
DR CONS             PRFLEQxKSECHFFNGTERVRFLDRYFYNQEEYVRFDSDVGEYRAVTELGRPDAEYWNSQKDLLEQRRAAVDTYCRHNYGVGESFTVQRR
DRB1*0702  (DB1)    -----W-G-YK----------Q--E-L----F------------------V--S-------I--D--GQ----V-----------
DRB1*0801  (MADURA) -----YSTG--Y---------------------------------------S---------F--D---L----------------
DRB1*0802  (SPL)    -----YSTG--Y--------------------------------------S-----------F--D---L----------------
DRB1*0803  (TAB)    -----YSTG--Y--------------------------------------S----------I--D---L----------------
DRB1*0804           -----YSTG--Y-------------------------------------------------F--D---L-------V--------
DRB1*0901  (Dw23)   ------------------Y-H-GI----N--------------------------------F--R---E---V------------
DRB1*1001           -----EV-F---------L-E-RVH-----A-Y---------------------------------R-------------------
DRB1*1101  (SVEIG)  -----YST-------------------------------F---------E------------F--D--------------------
DRB1*1102  (JVM)    -----YST-------------------------------F---------E------------F--D--------------------
DRB1*1103  (UA-S2)  -----YST-------------------------------F---------E------------I--DE------V------------
DRB1*1104  (TUBO)   -----YST-------------------------------F---------E------------F--DE------V------------
DRB1*1201  (HERLUF) -----YSTG--Y-------H-H--LL-------------F---------V--S---------I--D-------AV-----------
DRB1*1202           -----YSTG--Y-------H-H--LL-------------F---------V--S---------F--D-------AV-----------
DRB1*1301  (HHK)    -----YST-----------H-----N-------------F----------------------I--DE------V------------
DRB1*1302  (WT46)   -----YST-----------H-----N-------------F----------------------I--DE-------------------
DRB1*1303  (HAG)    -----YST-----------H-----N-------------F---------S------------I--DK-------------------
DRB1*1304           -----YST-----------H-----N-------------F---------S------------I--DE------V------------
DRB1*1305  (DES,DI) -----YST-----------H-----N-------------F----------------------F--D--------------------
DRB1*1401  (TEM)    -----YST-----------H-----F-------------F------------A--H------R--E--------------------
DRB1*1402  (AMALA)  -----YST----------E-H----N-------------F----------------------D--L--------------------
DRB1*1403  (JX6)    -----YST----------E-H----N-------------F----------------------D--L--------------------
```

TABLE 2-continued

```
                       10         20         30         40         50         60         70         80         90
                        *          *          *          *          *          *          *          *          *
DR CONS         PRFLEQxKSECHFFNGTERVRFLDRYFYNQEEYVRFDSDVGEYRAVTELGRPDAEYWNSQKDLLEQRRAAVDTYCRHNYGVGESFTVQRR
DRB1*1404       ----YSTG---------------H----F-----------------A--H-------R----E--------V-------
DRB1*1405       ---YST----Q------------H----F-----------------------------R----E--------V-
DRB3*0101 (52a) ----LR-------------Y----H----FL-----------------V--S-----------K-GR--N---------V---
DRB3*0201 (52b1)----LL-------------E-H-H-----A-----------R----------------K-GQ--N---------V---
DRB3*0202 (52b2)----LL-------------E-H-H-----A-----------R----------------K-GQ--N---------V---
DRB3*0301 (52c) ----LL-------------E---H-----F------------------V--S-----------K-GQ--N---------V---
DRB4*0101       ----A-C---L-----WN-I---I-----A-YN--L---Q-----------------R---E-----Y---V------
DRB5*0101 (Dw2) ----Q-D-Y----------H-DI-----DL-----------------------F--D-----------------
DRB5*0102 (Dw12)----Q-D-Y----------H-GI-----N------------------------F--D-----------------
DRB5*0201 (Dw21)----Q-D-Y----------H-GI-----N-------------------------------I---A---------AV---
DRB5*0202 (Dw22)----Q-D-Y----------H-GI-----N-------------------------------I---A---------AV---
```

TABLE 3

| DR cons | R F L E Q X K S E C H F F F N G T E R V R F L D R Y F Y N Q E E Y V R F D S D V G E Y R A |
| --- | --- |
| | 10              15              20              25              30              35              40              45 |
| | CACGTTTCTTGGAGCAGxxTAAGTCTGAGTGTCATTTCTTCAATGGACGGAGCGGGTGCGGTTCCTGGACAGATACTTCTATAACCAGGAGGAGTACGTGCGCTTCGACAGCGACGTGGGGAGTACCGGGCG |
| DRB3*0101 | --------------------T-CG------------------------------------------A-----------------T-C----------------------------------------- |
| DRB3*0201 | --------------------T-CT-------------------------------------------------G---C--------C---------------------------------------- |
| DRB3*0202 | --------------------T-CT-------------------------------------------------G---C--------C---------------------------------------- |
| DRB3*0301 | --------------------T-CT-------------------------------------------------G---C-----T--------------------------------------------|
| DRB1*0301 | --------------------T-CTC----C----------------------------------A--------G------A--------C------------------------T------------ |
| DRB1*0302 | --------------------T-CTC----C-------------------------------------------G------A--------C------------------------T------------ |
| DRB1*1101 | --------------------T-CTC----C-----------------------------------------------A-----------C------------------------T------------ |
| DRB1*1102 | --------------------T-CTC----C-----------------------------------------------A-----------C------------------------T------------ |
| DRB1*1103 | --------------------T-CTC----C-----------------------------------------------A-----------C------------------------T------------ |
| DRB1*1104 | --------------------T-CTC----C-----------------------------------A------------------------C------------------------T------------ |
| DRB1*1201 | --------------------T-CTC----C-GG--------------------------------A--------G---C--------CT-C----------------------T------------ |
| DRB1*1202 | --------------------T-CTC----C-GG--------------------------------A--------G---C--------CT-C----------------------T------------ |
| DRB1*1301 | -----------------T-CTC----C---------------------------------------------------------------C------------------------T------------ |
| DRB1*1302 | --------------------T-CTC----C-----------------------------------------------A-----------C------------------------T------------ |
| DRB1*1303 | --------------------T-CTC----C-----------------------------------------------A-----------C------------------------T------------ |
| DRB1*1304 | --------------------T-CTC----C-----------------------------------------------A-----------C------------------------T------------ |
| DRB1*1305 | --------------------T-CTC----C-----------------------------------------------A-----------C------------------------T------------ |
| DRB1*1401 | --------------------T-CTC----C-----------------------------------------------------------C------------------------T------------ |
| DRB1*1402 | --------------------T-CTC----C-----------------------------------------------A---G-------C------------------------T------------ |
| DRB1*1403 | --------------------T-CTC----C-----------------------------------------------A---G-------C------------------------T------------ |
| DRB1*1404 | --------------------T-CTC----C---------A------------------------------------------------C------------------------T------------ |
| DRB1*1405 | --------------------T-CTC----C-GG--------------------------------------------A-----------C------------------------T------------ |
| DRB1*0801 | --------------------T-CTC----C-GG--------------------------------------------A-----------C-------------------------------------- |
| DRB1*0802 | --------------------T-CTC----C-GG--------------------------------------------A-----------C-------------------------------------- |

TABLE 3-continued

| | 50 | 55 | 60 | 65 | 70 | 75 | 80 | 85 | 90 | |
|---|---|---|---|---|---|---|---|---|---|---|
| | V T E L G | R P D A E | Y W N S Q | K D L L E Q | X R A X V | D T Y C R | H N Y G V | G E S F T | V Q R R | |
| DR cons | GTGACGGAGCTGGGG | CGGCCTGGG | GAGTACTGG | AACAGCCAG | AAGGACCTC | CTGGAGCAG | AXGGGGCCG | xGGTGACAG | ACACCTAC | TGCAGACACAACTACGGGGTTGGTGAGAGCTTCACAGTGCAGCGGCGA |
| DRB1*0803 | ----------- | -T-CTC--C-GG | ------T-- | ---------- | ---------- | ---------- | ------A-- | ---A------ | ---------- | |
| DRB1*0804 | ----------- | -T-CTC--C-GG | ------T-- | ---------- | ---------- | ---------- | ---A------ | ---------- | ---------- | |
| DRB1*04 | ----------- | --GT--ACA-- | ---------- | ---------- | ---------- | ---------- | ------C--A | ---------- | ---------- | |
| DRB1*0406 | ----------- | --GT--ACA-- | ---------- | ---------- | ---------- | ---------- | ---C------ | ---------- | ---------- | |
| DRB4*0101 | ----------- | ----GC----- | ---G------ | ---------- | A--T-AA--AT | ------A--- | ---------- | ----C-A-A- | -T--C----- | |
| DRB1*07 | ----------- | --C--TG---- | GG----A--A | ---------- | ---------- | --A---CT-- | ----A----- | ---------- | ---------- | |
| DRB1*0901 | ----------- | ----------- | ---------- | ---------- | -----C---- | --AT--C--- | --GG-A---- | ------T--- | ---------- | |
| DRB1*1001 | ----------- | ---G--GT--- | -----T---A | ---------- | ---------- | ---G--A--- | --CG-G--C- | ---------- | ------A--- | |
| DRB1*0101 | ----------- | ---TG--CT-- | -----T---A | ---------- | -----C---- | ---G--A--- | -----A---- | ------C--- | ---------- | |
| DRB1*0102 | ----------- | ---TG--CT-- | -----T---A | ---------- | -----C---- | ---G--GA-- | -----A---- | ---------- | ---------- | |
| DRB1*0103 | ----------- | ---TG--CT-- | -----T---A | ---------- | -----C---- | ---G--GA-- | -----A---- | ------C--- | ---------- | |
| DRB5*0101 | ----------- | ----C--GA-- | -----A---- | ---------- | ----C----- | ------A--- | -----A---- | ------G--T | ---------- | |
| DRB5*0102 | ----------- | ----C--GA-- | -----A---- | ---------- | ---------- | ---------- | -----A---- | ---------- | ---------- | |
| DRB5*0201/02 | ----------- | ----C--GA-- | -----A---- | ---------- | ----C----- | ------A--- | --GG-A---- | ---------- | ---------- | |
| DRB1*1501 | ----------- | ----C--TG-- | --CC---AGG | ---------- | ---------- | ---------- | -----A---- | ------C--- | -------T-- | |
| DRB1*1502 | ----------- | ----C--TG-- | --CC---AGG | ---------- | ---------- | ---------- | ---------- | ------C--- | -------T-- | |
| DRB1*1601 | ----------- | ----C--TG-- | --CC---AGG | ---------- | ---------- | ---------- | ---------- | ------C--- | ---------- | |
| DRB1*1602 | ----------- | ----C--TG-- | --CC---AGG | ---------- | ---------- | ---------- | ---------- | ------C--- | ---------- | |
| DRB3*0101 | ----------- | ----------- | --TC------ | ---------- | ---A------ | ---G-CG--- | -------AT- | ---------- | ---------- | (SEQ ID NO:24) |
| DRB3*0201 | ---G------- | ----------- | ---------- | ---------- | ---A------ | ---G-CA--- | -------AT- | -------TG- | ---------- | |
| DRB3*0202 | ---G------- | ----------- | ---------- | ---------- | ---A------ | ---G-CA--- | -------AT- | ---------- | ---------- | |
| DRB3*0301 | ----------- | ----------- | --TC------ | ---------- | ---A------ | ---G-CA--- | -------AT- | -------TG- | ---------- | |
| DRB1*0301 | ----------- | ----------- | ---------- | ---------- | ---A------ | ---G-CG--- | ---------A | -------TG- | ---------- | |

TABLE 3-continued

| | | | | | | |
|---|---|---|---|---|---|---|
| DRB1*0302 | --------- | --------- | --------- | --------- | -A----G-CG-------A--------- | --------- |
| DRB1*1101 | --------- | -AG------ | --------- | ---T----- | -AG-C--G---------C--------- | --------- |
| DRB1*1102 | --------- | -AG------ | --------- | ---A----- | -AG-CGA----------C--------- | -TG------ |
| DRB1*1103 | --------- | -AG------ | --------- | ---T----- | -AG-CGA----------C--------- | -TG------ |
| DRB1*1104 | --------- | -AG------ | --------- | ---T----- | -AG-C--G---------C--------- | -TG------ |
| DRB1*1201 | --------- | -TC------ | ----C---- | ---A----- | -AG-C--G---------C-----T--- | -C--TG--- |
| DRB1*1202 | --------- | -TC------ | ----C---- | ---T----- | -AG-C--G---------C-----T--- | -C--TG--- |
| DRB1*1301 | --------- | --------- | --------- | ---A----- | -AG-CGA----------C--------- | -TG------ |
| DRB1*1302 | --------- | --------- | --------- | ---A----- | -AG-CGA----------C--------- | -TG------ |
| DRB1*1303 | --------- | -AGC----- | --------- | ---A----- | -AG-C-A----------C---G----- | --------- |
| DRB1*1304 | --------- | -AGC----- | --------- | ---A----- | -AG-CGA----------C--------- | -TG------ |
| DRB1*1305 | --------- | --------- | ---T----- | ---T----- | -AG-C--G---------C--------- | -TG------ |
| DRB1*1401 | --------- | -C--G--C- | --------- | --------- | ---G---------A---C-----T--- | -TG------ |
| DRB1*1402 | --------- | --------- | --------- | --------- | ---G-------------C--------- | --------- |
| DRB1*1403 | --------- | -AGC----- | --------- | --------- | -AG-C--G---------CT----T--- | --------- |
| DRB1*1404 | --------- | -C---G--C | --------- | ---G----- | ---G-------------A-----T--- | --------- |
| DRB1*1405 | --------- | ----T---- | --------- | --------- | ---G-------------A--------- | -TG------ |
| DRB1*0801 | --------- | -AGC----- | --------- | ---T----- | -AG-C--G---------CT-------- | -TG------ |
| DRB1*0802 | --------- | --------- | --------- | ---T----- | -AG-C--G---------CT-------- | -G------- |
| DRB1*0803 | --------- | -AGC----- | --------- | ---A----- | -AG-C--G---------CT-------- | --------- |
| DRB1*0804 | --------- | --------- | --------- | ---T----- | -----A-----------C--------- | -TG------ |
| DRB1*0401 | --------- | --------- | --------- | ---A----- | -AG-CGA----------C--------- | -TG------ |
| 0402 | --------- | --------- | --------- | --------- | ---G-------------A--------- | -TG------ |
| 0404 | --------- | --------- | --------- | --------- | ---G-------------C--------- | -TG------ |
| 0405 | --------- | -AGC----- | --------- | --------- | ---G-------------C--------- | --------- |

TABLE 3-continued

```
0406          ------------------------------------G-------A-------------TG----------
0407          ------------------------------------G-------A-------------------------
0408          ------------------------------------G-------C-------------------------
DRB4*0101     ------------C-T---------------------G-------A-------T-----TG----------
DRB1*07       ------A-----TC------C---------------G-C-G---G-CA--GTG-----------------
DRB1*0901     ------------T-------C---------------G-G-----A-----GTG-----------------
DRB1*1001     ----------------------------------------------------------------------
DRB1*0101     ------------G-------T---------------G-G-T---C-------------------------
DRB1*0102     ------------------------------------G-------C-------------C-TG--------
DRB1*0103     ------------A-----------------------AG-C-G---C-------------------------
DRB5*0101     ------------C-T---------------------AG-C-G---C-------------------------
DRB5*0102     ------------C-T---------------------AG-C-G---C-------------------------
DRB5*0201/02  ------------C-T---------------------GC------C-------------C-TG--------
DRB1*1501     ------------C-T---------------------GC------C-------------TG----------
DRB1*1502     ------------C-T---------------------GC------C-------------------------
DRB1*1601     ------------C-T---------------------AG-C-G---C-------------------------
DRB1*1602     ------------C-T---------------------AG-C-G---C-------------------------
```

EXAMPLE 4

Using the 2 protocols described above, oligonucleotides were synthesized either carrying a ligand, as described in Example 1 and which are summarized in Table 4, or coupled to BSA, as described in Example 2 and which are summarized in Table 5.

TABLE 4

| Ref. | No. | 5'-3' sequence *** | | ligand X | tr ** |
|---|---|---|---|---|---|
| 1 | 563 | CTGGAAAGATGCA | (SEQ ID NO:25) | a | 17.11 |
| 2 | 562 | TGGAAAGATGCAT | (SEQ ID NO:26) | a | 17.63 |
| 3 | 561 | CAGGATAAGTATGA | (SEQ ID NO:27) | a | 17.52 |
| 4 | 579 | GCAGGATAAGTATGA | (SEQ ID NO:28) | a | 16.7 |
| 5 | 603 | CAGCAGGATAAGTATG | (SEQ ID NO:29) | b | 17.44 |
| 6 | 1094 | CAGCAGGATAAGTATG | (SEQ ID NO:29) | a | 16.25 |
| 7 | 546 | TGGACAACTACTG | (SEQ ID NO:30) | a | 18.61 |
| 7a | 570 | GGACAACTACTG | (SEQ ID NO:31) | a | 16.09 |
| 8 | 596 | GGACAACTACTG | (SEQ ID NO:31) | b | 17.29 |
| 9 | 545 | GATACTTCTATCACC | (SEQ ID NO:32) | a | 19.2 |
| 10 | 398 | CCTGATGAGGAGTA | (SEQ ID NO:33) | a | 14.6 |
| 11 | 573 | CAGGGTAAGTATAAG | (SEQ ID NO:34) | a | 16.18 |
| 12 | 580 | GCAGGGTAAGTATAAG | (SEQ ID NO:35) | a | 16.99 |
| 13 | 1064 | TGGCAGGGTAAGTAT | (SEQ ID NO:36) | a | 17.55 |
| 14 | 591 | GGCAGGGTAAGTATAAG | (SEQ ID NO:37) | b | 18.18 |
| 15 | 1095 | GGCAGGGTAAGTATAAG | (SEQ ID NO:37) | a | 17.13 |
| 16 | 400 | GGCCCTGGTGGA | (SEQ ID NO:38) | a | 13.79 |
| 17 | 595 | GGCCCTGGTGGA | (SEQ ID NO:38) | b | 17.43 |
| 18 | 574 | GCGGTATCTGCACA | (SEQ ID NO:39) | a | 16.62 |
| 19 | 556 | GGAGGAGGTTAAG | (SEQ ID NO:40) | a | 17.94 |
| 20 | 555 | TGGAAGACGAGC | (SEQ ID NO:41) | a | 16.1 |
| 21 | 755 | TGCGGAGCACTGGA | (SEQ ID NO:42) | a | 16.85 |
| 22 | 867 | GGAAGACAAGCG | (SEQ ID NO:42) | a | 13.36 |
| 23 | 915 | CTCTACGGGTGAG | (SEQ ID NO:43) | a | 19.04 |
| 24 | 1066 | CTCTACGGGTGAGT | (SEQ ID NO:44) | a | 17.14 |
| 25 | 990 | CACCTATTGCAGA | (SEQ ID NO:45) | a | 17.47 |
| 26 | 1067 | CACCTATTGCAGAC | (SEQ ID NO:46) | a | 17.08 |
| 27 | 1068 | ACACCTATTGCAGA | (SEQ ID NO:47) | a | 17.81 |
| 28 | 802 | CCAGGAGGAGAACGT | (SEQ ID NO:48) | a | 15.86 |
| 29 | 1096 | CCAGGAGGAGAACGT | (SEQ ID NO:48) | c | 15.77 |
| 30 | 1097 | CCAGGAGGAGAACGT | (SEQ ID NO:48) | d | 13.74 |
| 31 | 1098 | CCAGGAGGAGAACGT | (SEQ ID NO:48) | e | 14.03 |
| 32 | 1099 | CCAGGAGGAGAACGT | (SEQ ID NO:48) | f | 14.81 |
| 33 | 1100 | CCAGIAGGAGAACGT | (SEQ ID NO:49) | a | 14.97 |
| 34 | 1107 | ACCAGIAGGAGAACGT | (SEQ ID NO:50) | a | 16.05 |

TABLE 4-continued

| Ref. | No. | 5'-3' sequence *** | | ligand X | tr ** |
|---|---|---|---|---|---|
| 34a | 1127 | AACCAGIAGGAGAACGT | (SEQ ID NO:17) | a | 16.62 |
| 35 | 935 | ACCAGGAGGAGAACGTG | (SEQ ID NO:14) | - | 19.29 |
| 36 | 997 | GAGCTGCGTAAG | (SEQ ID NO:51) | a | 16.55 |
| 37 | 1033 | TTCCTGGAGAGACAC | (SEQ ID NO:21) | a | 18.4 |
| 38 | 1030 | TTCCTGGAGAGATAC | (SEQ ID NO:52) | a | 18.39 |
| 39 | 1065 | TCCTGGAGAGATACT | (SEQ ID NO:53) | a | 18.01 |
| 40 | 1058 | GGAGGACTTGCGC | (SEQ ID NO:54) | a | 17.9 |
| 41 | 1059 | GGAGGACTTGCGCT | (SEQ ID NO:55) | a | 18.35 |
| 42 | 1060 | AGGAGGACTTGCGC | (SEQ ID NO:56) | a | 17.05 |
| 42a | 1061 | ACGGGCTGTGGA | (SEQ ID NO:57) | a | 16.79 |

\* X represents the ligand according to the nomenclature used previously in Table 1
\*\* Tr represents the retention time in minutes (min) of the oligonucleotide in HPLC under the conditions described in Example 1 (BROWNLEE RP 18 column (4.6 mm × 25 cm), flow rate 1 ml/min).
\*\*\* The letter I in the sequences 33, 34 and 34a represents inosine.

TABLE 5

| REFERENCE | NUMBER | 5'—3' SEQUENCE | | TR * | OLIGO/BSA RATIO ** |
|---|---|---|---|---|---|
| 43 | 571B | TGGACAACTACT | (SEQ ID NO:58) | 7.85 (2M) | 1 |
| 44 | 574B | GCGCTATCTGCACA | (SEQ ID NO:39) | 8.69 (2M) | 0.8 |
| 45 | 556B | GGAGGAGGTTAAG | (SEQ ID NO:40) | 7.76 (2M) | 1 |
| 46 | 555B | TGGAAGACGAGC | (SEQ ID NO:41) | 16.85 (1M) | 0.8 |
| 47 | 756B | GCGGAGCACTGG | (SEQ ID NO:59) | 17.78 (1M) | 1.5 |
| 48 | 867B | GGAAGACAAGCG | (SEQ ID NO:42) | 16.65 (1M) | 1.1 |
| 49 | 868B | TGGAAGACAAGC | (SEQ ID NO:60) | 8.56 (2M) | 1.3 |
| 50 | 856B | GAGGAGCTCCTGCGCT | (SEQ ID NO:61) | 19.96 (1M) | 1.2 |
| 51 | 966B | AGGAGAACGTGC | (SEQ ID NO:62) | 19.66 (1M) | 1.5 |
| 52 | 997B | GAGCTGCGTAAG | (SEQ ID NO:51) | 18.88 (1M) | 0.9 |
| 53 | 998B | AGCTGCGTAAGT | (SEQ ID NO:63) | 16.32 (1M) | 1 |
| 54 | 1026B | GAGAGACACTTCC | (SEQ ID NO:64) | 13.98 (1M) | 0.5 |
| 55 | 986B | GGAGAGATACTTC | (SEQ ID NO:65) | 15.81 (1M) | 0.6 |
| 56 | 1049B | GAGAGATACTTCC | (SEQ ID NO:66) | 15.86 (1M) | 1.2 |
| 57 | 1089B | ACGGGCTGTG | (SEQ ID NO:67) | 17.72 (1M) | 1.1 |
| 58 | 1090B | TACGGGCTGT | (SEQ ID NO:68) | 17.24 (1M) | 1 |
| 59 | 1091B | CGGGGCTGTGG | (SEQ ID NO:69) | 17.42 (1M) | 1.1 |

\* Tr represents the retention time in minutes (min) of the oligonucleotide coupled to BSA in HPLC under the conditions described in Example 2.
(1M) means that the buffer B contains 1M NaCl.
(2M) means that the buffer B contains 2M NaCl.
\*\* The oligonucleotide is quantified in picomoles by UV spectrometry, measuring the absorbance at 260 nm according to the APPLIED BIOSYSTEMS protocol. BSA is assayed by the method of BRADFORD (BRADFORD M.M., Anal. Biochem., 72,248 (1976)) in picomoles. The oligo/BSA ratio is the ratio of these 2 values.

In this example, capture oligonucleotides which can be synthesized without a ligand or with a ligand or alternatively coupled, for example, to BSA have been defined. The choice of the sequences of the oligonucleotides synthesized takes account of the alignment of the DNA sequences of the different alleles described in Table 3 of Example 3. The oligonucleotide probes selected, used, for example, as capture probes, enable a typing plan to be constructed, as described in Table 6. It is quite obvious to a person skilled in the art that other typing plans may be defined with other oligonucleotides.

In Table 6, the designations between brackets represent the nomenclature used before the Conference on Histocompatibility (1991) for the subtypes of the DRB5 allele.

The + sign means that the subtype of the line in question in Table 6 gives a hybridization with the probe in the corresponding column.

Using Table 6, it is possible to interpret readily the results obtained (hybridization or lack of hybridization) with various probes, for example a target giving a positive response with the probes 43, 14, 28 and 37 corresponds to the types DRB1*0301/DRB1*07.

TABLE 16

| probe type | 1 | 5 | 43 | 9 | 10 | 14 | 17 | 44 | 45 | 46 | 48 | 47 | 28 | 24 | 27 | 52 | 37 | 55 | 42 | 42a |
|---|---|---|---|---|---|---|---|---|---|---|---|---|---|---|---|---|---|---|---|---|
| DRB1*0101 | + | | | | | | | | | | | | | | | | | | | |
| DRB1*0102 | + | | | | | | | | | | | | | | | | | | | + |
| DRB1*0103 | + | | | | | | | | | + | | | | | | | | | | |
| DRB5*0101 | | + | | | | | | | | | | | | | | | + | | | |
| DRB5*0102 | | + | | | | | | | | | | | | | | | | | | |
| DRB5*0201/0202 | | + | | | | | | | | | | | | | | | | | | + |
| DRB1*0301 | | | + | | | | | | | | | | + | | | | + or + | | | |
| DRB1*0302 | | | + | | | | | | | | | | + | | | | + | + | | |
| DRB1*0401–0412 | | | | + | | | | | | | | | | | | | | | | |
| DRB1*0402 | | | | + | | | | | | + | | | | | | | | | | |
| DRB1*1101/1104 | | | | | + | | | | | | | | | | | | + | | | |
| DRB1*1102/1103 | | | | | + | | | | | + | | | | | | | + | | | |
| DRB1*1201/1202 | | | | | | | | | | | | | | + | + | | + | | | + |
| DRB1*1301 | | | | | | + | | | | | | | + | | | | + or + | | | |
| DRB1*1302 | | | | | | + | | | | | | | + | | | | | + | | |
| DRB1*1303 | | | | | | | + | | | | | | | | | | + | | | |
| DRB1*1304 | | | | | | + | | | | | | | | | | | + | | | |
| DRB1*1305 | | | | | | | | | | | | | + | | | | + | | | |
| DRB1*1401 | | | | | | | | | | | | | | + | | | + | + | | |
| DRB1*1402 | | | | | | | | | | | | | + | | | | + | + | | |
| DRB1*1403 | | | | | | | + | | | | | | + | | | | + | + | | |
| DRB1*1404 | | | | | | | | | | | | + | | + | + | | + | | | |
| DRB1*1405 | | | | | | | | | | | | | | | | | + | + | | |
| DRB1*0701/0702 | | | | | + | | | | | | | | | | | | | | | |
| DRB1*0801–0804 | | | | | | + | | | | | | | | | + | | | | | |
| DRB1*0901 | | | | | | | + | | | | | | | | | | | | | |
| DRB1*1001 | | | | | | | | + | | | | | | | | | | | | |

EXAMPLE 5

Preparation of Detection Probes

According to Example 2, the oligonucleotide, activated and dried under vacuum, is taken up with $1.25 \times 10^{-7}$ mol (5 mg) of horseradish peroxidase (BOEHRINGER MANHEIM 413470) in 200 μl of 0.1M sodium borate buffer, pH 9.3.

The purification protocol is identical: the conjugate is stored at −20° C. in 50 mM Tris-HCl buffer, pH 7.0, 40% glycerol.

Table 7 summarizes the different conjugates used for HLA-DR detection.

TABLE 7

| REFERENCE | 5'—3' SEQUENCE *** | | TR * | OLIGO/-HRP RATIO ** |
|---|---|---|---|---|
| D1 | CCGGGCGGTGAC(GT)GAGCTGGGGC | (SEQ ID NO:70) | 11.88 (2M) | 1.4 |
| D2 | CCGGGCGGTGACIGAGCTGGGGC | (SEQ ID NO:71) | 18.09 (2M) | 1.8 |

TABLE 7-continued

| REFERENCE | 5'—3' SEQUENCE *** | | TR * | OLIGO/-HRP RATIO ** |
|---|---|---|---|---|
| D3 | GAACAGCCAGAAGGAC | (SEQ ID NO:72) | 9.32 (2M) | 1 |

* Tr represents the retention time in minutes (min) of the oligonucleotide coupled to horseradish peroxidase (HRP) in HPLC under the conditions described in Example 2.
(2M) means that the buffer B contains 2M NaCl.
** The oligonucleotide is quantified in picomoles by UV spectrometry, measuring the absorbance at 260 nm according to the APPLIED BIOSYSTEMS protocol. Horseradish peroxidase (HRP) is assayed by UV at 402 nm in picomoles according to ATOR M.A., J. Biol. Chem., 31,14954 (1987). The oligo/HRP ratio is the ratio of these 2 values.
*** the letter I in the sequence D2 represents inosine. In the sequence D1, (GT) means that there is an equimolar mixture of the 2 bases G and T at this position.

EXAMPLE 6

Preparation of Genetic Material

The extraction of nucleic acids from whole blood is performed in an Applied Biosystems apparatus according to the following protocol: 2 to 6 ml of whole blood are taken up in TE buffer (10 mM Tris-HCl, pH 8.00, 1 mM EDTA) (quantity sufficient for 6 ml) and are placed in a 30-ml extraction funnel. A solution of proteinase K (840 units in 20 mM Tris-HCl, pH 8.5) is added. The whole is incubated with agitation for 1 hour at 55° C. The excess of proteins present is removed by 2 simultaneous extractions (8.5 ml) with a phenol/chloroform mixture. The whole is agitated for 20 minutes at 60° C. After removal of the organic phase, a further phenol extraction is performed. The excess phenol is removed by an extraction with chloroform (9.5 ml) for 10 minutes at 37° C. The DNA content in the aqueous phase is precipitated by adding 0.5 ml of 3M sodium acetate, pH 5.5 and 13.5 ml of isopropanol, and then recovered on a filter. The DNA is then taken up in 1 ml of distilled water and thereafter assayed by spectrophotometry at 260 nm.

EXAMPLE 7

Amplification of the DNA

Enzymatic amplification is performed by the polymerase chain reaction (PCR) technique (MULLIS and FALOONA, Meth. in Enzymol. vol. 155, pp 335–350) according to the following protocol:

0.1 to 2 µg of DNA, purified or otherwise, in a total volume of 100 µl of the following buffer are added into an Eppendorf type tube:

10 µl of 10-fold concentrated PCR buffer (500 mM KCl, 100 mM Tris-HCl, pH 8.3 (20° C.), 15 mM MgCl$_2$, 0.1% gelatin)

2 µl of 0.5 µM dNTP (dATP, dCTP, dGTP, TTP)

2 µl of each primer corresponding to 25 pmol 1.5 units of Taq polymerase (Perkin Elmer Cétus)

distilled water (quantity sufficient for 100 µl)

50 µl of paraffin oil

The tube is placed in a Thermocycler (Perkin Elmer Cétus) in which the following 35 temperature cycles will be performed:

0.5 minute of denaturation at 95° C.

0.5 minute of hybridization at 55° C.

0.5 minute of elongation at 72° C.

The primers used have the following sequence:

primer 1=5'-CCGGATCCTTCGTGTCCCCA-CAGCACG-3' (SEQ ID NO: 73)

primer 2=5'-TCGCCGCTGCACTGTGAAG-3' (SEQ ID NO: 74)

EXAMPLE 8

100 µl of a solution of a capture oligonucleotide of a given DR specificity at a concentration of 0.15 µM in 3×PBS (0.45M NaCl, 0.15M sodium phosphate, pH 7.0) are deposited in a well of a polystyrene microtitration plate (Nunc 439454). The number of wells filled is equal to that needed for the typing.

In all cases, a positive control should be added for the purpose of checking the efficiency of the amplification step and also the detection step. The capture probe which is used as positive control is present on all the alleles known to date, and has the following sequence:

5'-GGGGAGTACCGGGCGGTGACGGAGCTGGGG-CGGCCT-3' (SEQ ID NO:75)

The plate is washed 3 times with 300 µl of PBS/Tween (0.15M NaCl, 0.05M sodium phosphate, pH 7.0; 0.5% Tween 20 (Merck 822184)). The amplification product (100 µl) as described in Example 7 is denatured with 10 µl of 2N NaOH for 5 minutes with agitation at room temperature. 10 µl of 2N acetic acid and then a volume of PEG buffer (0.1M sodium phosphate, pH 7.0, 0.5M NaCl, 0.65% Tween 20, 0.14 mg/ml salmon sperm DNA (Sigma D 9156), 2% PEG 4,000 (Merck 807490)) equivalent to n×50 µl (n being the number of capture probes needed for the typing) are added successively to this solution. 50 µl of this solution are distributed per well, followed by 50 µl of the detection probe (oligonucleotideperoxidase conjugate) at a concentration of 15 nM in the PEG buffer. The plate is incubated for 1 h at 37° C. and washed with 3×300 µl of PBS/Tween. 100 µl of OPD substrate (ortho-phenylenediamine, Cambridge Medical Biotechnology ref/456) in an OPD buffer (0.05M citric acid, 0.1M Na$_2$HPO$_4$, pH 4.93) at a concentration of 4 mg/ml, to which "30 volumes" H$_2$O$_2$ at a dilution of 1/1000 is added immediately before use, are added per well. After 20 min of reaction, the enzyme activity is blocked with 100 µl of 1N H$_2$SO$_4$, and reading is performed on an Axia Microreader (bioMérieux) at 492 nm.

EXAMPLE 9

6DNAS, prepared according to the method described in Example 6, are amplified according to the method described in Example 7.

The typing protocol contains the following capture probes:

5' a-GATACTTCTATCACC (SEQ ID NO:32)³'= oligonucleotide of specificity DR 3 carrying the ligand a at the 5' end (bearing reference 545)

5' GATACTTCTATCACC (SEQ ID NO:32)³'= oligonucleotide of identical sequence but without ligand (bearing reference 545 nu)

5' a-TGGACAACTACTG (SEQ ID NO:30)³'= oligonucleotide of specificity DR 4 carrying the ligand a at the 5' end (bearing reference 546)

5' TGGACAACTACTG (SEQ ID NO:30)³'= oligonucleotide of identical sequence but without ligand (bearing reference 546 nu)

The typing protocol is in accordance with the general protocol described in Example 8.

The probes D1 and D2 (Table 7) are used in a 50%/50% mixture as detection probes.

The results are presented in Table 8 below:

TABLE 8

| DNA | TYPING | DR3 545 NU | DR3 545 | DR4 546 NU | DR4 546 |
|---|---|---|---|---|---|
| 1 | DR11/DR11 | 0.019 | 0.025 | 0.021 | 0.025 |
| 2 | DR4/DR4 | 0.018 | 0.021 | 0.021 | 0.138 |
| 3 | DR8/DR7 | 0.017 | 0.022 | 0.019 | 0.019 |
| 4 | DR3/DR11 | 0.026 | 0.423 | 0.021 | 0.027 |
| 5 | DR3/DR4 | 0.023 | 0.176 | 0.026 | 0.296 |
| 6 | DR3/DR3 | 0.023 | 0.387 | 0.023 | 0.018 |

The 2 capture probes without ligand do not differentiate the specificities of the DNAs, whereas the same sequences with the ligand a enable the DR2 and DR4 specificities of the DNAs to be identified.

EXAMPLE 10

24 DNAs, prepared according to the method described in Example 6, are amplified according to the method described in Example 7.

The typing protocol is in accordance with the general protocol described in Example 8.

The probes D1 and D2 (Table 7) are used in a 50%/50% mixture as detection probes.

The typing protocol contains the capture probes summarized in Table 9 below.

TABLE 9

| reference | number | 5'-3' sequence | |
|---|---|---|---|
| 1 | 563 | CTGGAAAGATGCA | (SEQ ID NO:25) |
| 5 | 603 | CAGCAGGATAAGTATG | (SEQ ID NO:29) |
| 43 | 571B | TGGACAACTACT | (SEQ ID NO:58) |
| 9 | 545 | GATACTTCTATCACC | (SEQ ID NO:32) |
| 10 | 398 | CCTGATGAGGAGTA | (SEQ ID NO:33) |
| 14 | 591 | GGCAGGGTAAGTATAAG | (SEQ ID NO:37) |
| 17 | 595 | GGCCCTGGTGGA | (SEQ ID NO:38) |
| 44 | 574B | GCGGTATCTGCACA | (SEQ ID NO:39) |
| 45 | 556B | GGAGGAGGTTAAG | (SEQ ID NO:40) |
| 46 | 555B | TGGAAGACGAGC | (SEQ ID NO:41) |
| 48 | 867B | GGAAGACAAGCG | (SEQ ID NO:42) |
| 47 | 756B | GCGGAGCACTGG | (SEQ ID NO:59) |
| 28 | 802 | CCAGGAGGAGAACGT | (SEQ ID NO:48) |
| 24 | 1066 | CTCTACGGGTGAGT | (SEQ ID NO:44) |
| 27 | 1068 | ACACCTATTGCAGA | (SEQ ID NO:47) |
| 52 | 997B | GAGCTGCGTAAG | (SEQ ID NO:51) |
| 37 | 1033 | TTCCTGGAGAGACAC | (SEQ ID NO:21) |
| 55 | 986B | GGAGAGATACTTC | (SEQ ID NO:65) |
| 42 | 1060 | AGGAGGACTTGCGC | (SEQ ID NO:56) |

The results of the typing are given in Table 10:

TABLE 10

| | PROBE | | | | | | | | | | | |
|---|---|---|---|---|---|---|---|---|---|---|---|---|
| | 1 | 5 | 43 | 9 | 10 | 14 | 17 | 44 | 45 | 46 | 48 | 47 |
| | | | | | | | | OLIGO No. | | | | |
| DNA No. | 563 | 603 | 571-BSA | 545 | 398 | 591 | 595 | 574-BSA | 556-BSA | 555-BSA | 867-BSA | 756-BSA |
| 58 | 0.017 | 0.025 | 0.718 | 0.013 | 0.029 | 1.006 | 0.072 | 0.033 | 0.022 | 0.018 | 0.015 | 0.016 |
| 59 | 0.509 | 0.024 | 0.036 | 0.016 | 0.029 | 0.929 | 0.072 | 0.031 | 0.025 | 0.018 | 0.037 | 0.018 |
| 63 | 0.014 | 0.021 | 0.030 | 0.011 | 0.024 | 0.050 | 0.030 | 0.033 | 0.023 | >2.500 | 0.016 | 0.024 |
| 66 | 0.012 | 0.027 | 0.066 | 0.015 | 0.023 | 0.992 | 0.098 | 0.031 | 0.024 | 0.022 | 0.060 | 0.016 |
| 67 | 0.468 | 0.089 | 0.035 | 0.042 | >2.500 | 0.054 | 0.030 | 0.032 | 0.028 | >2.500 | 0.042 | 0.015 |
| 68 | 0.017 | 0.049 | 0.037 | 0.025 | 0.017 | 0.826 | 0.068 | 0.031 | 0.024 | >2.500 | 0.120 | 0.016 |
| 70 | 0.504 | 0.018 | 0.027 | 0.020 | 0.076 | 0.016 | 0.017 | 0.033 | 0.031 | 0.017 | 0.070 | 1.674 |
| 71 | 0.011 | 0.017 | 0.031 | 0.025 | >2.500 | 0.019 | 0.030 | 0.032 | 0.030 | >2.500 | 0.020 | 0.021 |
| 72 | 0.459 | 1.373 | 0.046 | 0.025 | 0.031 | 0.085 | 0.015 | 0.044 | 0.037 | 0.017 | 0.017 | 0.019 |
| 73 | 0.353 | 0.890 | 0.034 | 0.018 | 0.016 | 0.048 | 0.021 | 0.044 | 0.034 | 0.019 | 0.015 | 0.017 |
| 75 | 0.019 | 0.052 | 0.625 | 1.113 | 0.044 | 0.043 | 0.023 | 0.033 | 0.038 | 0.019 | 0.018 | 0.017 |

TABLE 10-continued

| | | | | | | | | | | | | |
|---|---|---|---|---|---|---|---|---|---|---|---|---|
| 78 | 0.015 | 0.037 | 0.625 | 0.015 | 0.032 | 0.589 | 0.046 | 0.034 | 0.031 | 0.015 | 0.048 | 0.019 |
| 79 | 0.014 | 0.012 | 0.425 | 0.013 | 0.030 | 0.010 | 0.015 | 0.033 | 0.028 | >2.500 | 0.039 | 0.017 |
| 80 | 0.018 | 0.752 | 0.041 | 0.025 | 0.016 | 0.448 | 0.040 | 0.045 | 0.030 | 0.021 | 0.036 | 0.016 |
| 83 | 0.014 | 0.959 | 0.030 | 0.022 | 0.017 | 0.042 | 0.536 | 0.050 | 0.028 | 0.073 | 0.023 | 0.021 |
| 84 | 0.007 | 0.013 | 0.023 | 0.399 | 0.015 | 0.013 | 0.014 | 0.031 | 0.028 | 1.210 | 0.042 | 0.016 |
| 85 | 0.015 | 0.013 | 0.468 | 0.014 | 0.010 | 0.018 | 0.016 | 0.076 | 0.034 | >2.500 | 0.012 | 0.019 |
| 86 | 0.019 | 0.747 | 0.035 | 0.939 | 0.023 | 0.056 | 0.018 | 0.041 | 0.029 | 0.021 | 0.070 | 0.021 |
| 87 | 0.016 | 1.190 | 0.035 | 0.016 | 0.013 | 0.046 | 0.014 | 0.043 | 0.029 | >2.500 | 0.025 | 0.019 |
| 89 | 0.012 | 0.032 | 0.026 | 0.956 | 0.015 | 0.021 | 0.018 | 0.032 | 0.028 | 0.017 | 0.014 | 0.019 |
| 90 | 0.355 | 0.035 | 0.031 | 1.028 | 0.042 | 0.038 | 0.023 | 0.035 | 0.036 | 0.017 | 0.016 | 0.022 |
| 91 | 0.866 | 0.008 | 0.016 | 0.014 | 0.040 | 0.036 | 0.015 | 0.014 | 0.032 | 0.020 | 0.018 | 0.019 |
| 92 | 0.401 | 0.015 | 0.019 | 0.013 | 0.010 | 0.012 | 0.026 | 0.021 | 0.019 | 0.018 | 0.014 | 0.025 |
| 95 | 0.010 | 0.011 | 0.048 | 0.037 | 0.010 | 0.017 | 0.023 | 0.042 | 0.016 | 1.931 | 1.973 | 0.024 |

| | PROBE | | | | | | | | |
|---|---|---|---|---|---|---|---|---|---|
| | 28 | 24 | 27 | 52 | 37 | 55 | 42 | | |
| | OLIGO No. | | | | | | | | |
| DNA No. | 802 | 1066 | 1068 | 997-BSA | 1033 | 986-BSA | 1060 | +control | DNA No. | TYPING |
| 58 | 0.083 | 0.026 | 0.026 | 0.050 | 0.759 | 0.028 | 0.024 | >2.500 | 58 | DRBl*0301/DRB1*07 |
| 59 | 0.020 | 0.022 | 0.039 | 0.048 | 0.023 | 0.023 | 0.019 | >2.500 | 59 | DRBl*0101–0102/DRB1*07 |
| 63 | 0.083 | 0.881 | 0.584 | 0.777 | 1.194 | 0.026 | 0.030 | >2.500 | 63 | DRBl*12/DRB1*1301 |
| 66 | 0.024 | 0.023 | 0.015 | 0.036 | 0.030 | 0.025 | 0.022 | >2.500 | 66 | DRB1*07/— |
| 67 | 0.028 | 0.028 | 0.032 | 0.041 | 0.893 | 0.026 | 0.026 | >2.500 | 67 | DRB1*01/DRB1*11 |
| 68 | 0.107 | 0.015 | 0.039 | 0.050 | 0.105 | 0.214 | 0.025 | >2.500 | 68 | DRB1*07/DRB1*1302 |
| 70 | 0.024 | 0.028 | 0.846 | 0.058 | 0.952 | 0.028 | 0.024 | >2.500 | 70 | DRB1*1401/DRB1*0101–0102 |
| 71 | 0.088 | 0.022 | 0.046 | 0.058 | 2.363 | 0.048 | 0.023 | >2.500 | 71 | DRB1*11/DRB1*1301 |
| 72 | 0.028 | 0.024 | 0.042 | 0.074 | 0.070 | 0.017 | 0.446 | >2.500 | 72 | DRB1*0101/DRB5*0101 |
| 73 | 0.024 | 0.023 | 0.030 | 0.135 | 0.045 | 0.018 | 0.424 | >2.500 | 73 | DRB1*0101/DRB5*0101 |
| 75 | 0.099 | 0.029 | 0.025 | 0.729 | 0.031 | 0.017 | 0.021 | >2.500 | 7s | DRB1*0301/DRB1*04 |
| 78 | 0.095 | 0.013 | 0.026 | 0.060 | 0.813 | 0.015 | 0.020 | >2.500 | 78 | DRB1*0301/DRB1*07 |
| 79 | 0.117 | 0.028 | 0.034 | 0.744 | 0.912 | 0.019 | 0.019 | >2.500 | 79 | DRB1*0301/DRB1*1301 |
| 80 | 0.030 | 0.021 | 0.066 | 0.040 | 0.045 | 0.014 | 0.412 | >2.500 | 80 | DRB1*07/DRB5*0101 |
| 83 | 0.040 | 2.096 | 0.060 | 0.038 | 0.058 | 0.023 | 0.501 | >2.500 | 83 | DRB1*08/DRB5*0101 |
| 84 | 0.152 | 0.021 | 0.049 | 0.041 | 0.011 | 0.210 | 0.019 | >2.500 | 84 | DRB1*04/DRB1*1302 |
| 85 | 0.219 | 0.070 | 0.040 | 0.612 | 0.038 | 0.168 | 0.024 | >2.500 | 85 | DRB1*03/DRB1*13 |
| 86 | 0.030 | 0.024 | 0.055 | 0.100 | 0.036 | 0.034 | 0.022 | >2.500 | 86 | DRB1*04/DRB5*0201–0202 |
| 87 | 0.183 | 0.048 | 0.096 | 0.595 | 0.047 | 0.015 | 0.024 | >2.500 | 87 | DRB1*1301/DRB5*0201–0202 |
| 89 | 0.026 | 0.617 | 0.301 | 0.042 | 0.567 | 0.019 | 0.024 | >2.500 | 89 | DRB1*04/DRB1*12 |
| 90 | 0.026 | 0.024 | 0.032 | 0.042 | 0.016 | 0.018 | 0.026 | >2.500 | 90 | DRB1*0101/DRB1*04 |
| 91 | 0.028 | 0.026 | 0.042 | 0.048 | 0.032 | 0.014 | 0.025 | >2.500 | 91 | DRB1*0101/— |
| 92 | 0.156 | 0.039 | 0.028 | 1.157 | 0.021 | 0.312 | 0.023 | >2.500 | 92 | DRB1*0101/DRB1*1402 |
| 95 | 0.154 | 0.079 | 0.028 | 1.224 | 0.023 | 0.302 | 0.022 | >2.500 | 95 | DRB1*1302/DRB1*1303 |

The method described enables us to type unambiguously the 24 DNAs tested.

EXAMPLE 11

The preferred hybridization temperature for the HLA-DR typing described in the present invention is 37° C. It is, however, possible to change this hybridization temperature.

The example which follows is identical to Example 10 except for the hybridization temperature, which has been changed from 37° C. to 45° C. Typing is carried out on 11 DNAs.

The capture probes used are given in Table 11 below:

TABLE 11

| reference | number | 5'–3' sequence | |
|---|---|---|---|
| 1 | 563 | CTGGAAAGATGCA | (SEQ ID NO:25) |
| 5 | 603 | CAGCAGGATAAGTATG | (SEQ ID NO:29) |
| 43 | 571B | TGGACAACTACT | (SEQ ID NO:58) |
| 9 | 545 | GATACTTCTATCACC | (SEQ ID NO:32) |
| 10 | 398 | CCTGATGAGGAGTA | (SEQ ID NO:33) |

TABLE 11-continued

| reference | number | 5'–3' sequence | |
|---|---|---|---|
| 14 | 591 | GGCAGGGTAAGTATAAG | (SEQ ID NO:37) |
| 17 | 595 | GGCCCTGGTGGA | (SEQ ID NO:38) |
| 44 | 574B | GCGGTATCTGCACA | (SEQ ID NO:39) |
| 45 | 556B | GGAGGAGGTTAAG | (SEQ ID NO:40) |
| 46 | 555B | TGGAAGACGAGC | (SEQ ID NO:41) |
| 48 | 867B | GGAAGACAAGCG | (SEQ ID NO:42) |
| 47 | 756B | GCGGAGCACTGG | (SEQ ID NO:59) |
| 28 | 802 | CCAGGAGGAGAACGT | (SEQ ID NO:48) |

The results of the typing are given in Table 12 below:

TABLE 12

| | PROBE | | | | | | | | |
|---|---|---|---|---|---|---|---|---|---|
| | 1 | 5 | 43 | 9 | 10 | 14 | 17 | 44 | 45 |
| | | | | | OLIGO No. | | | | |
| DNA No. | 563 | 603 | 571-BSA | 545 | 398 | 591 | 595 | 574-BSA | 556-BSA |
| 71 | 0.003 | 0.003 | 0.025 | 0.006 | 0.805 | 0.004 | 0.008 | 0.003 | 0.033 |
| 72 | 0.099 | 1.200 | 0.035 | 0.002 | 0.005 | 0.012 | 0.007 | 0.008 | 0.039 |
| 73 | 0.099 | 1.035 | 0.023 | 0.001 | 0.007 | 0.012 | 0.007 | 0.009 | 0.036 |
| 75 | 0.005 | 0.022 | 0.114 | 0.171 | 0.009 | 0.013 | 0.009 | 0.004 | 0.040 |
| 78 | 0.005 | 0.014 | 0.126 | 0.001 | 0.006 | 0.704 | 0.008 | 0.003 | 0.037 |
| 79 | 0.007 | 0.005 | 0.148 | 0.006 | 0.007 | 0.007 | 0.009 | 0.005 | 0.036 |
| 80 | 0.007 | 1.135 | 0.025 | 0.003 | 0.008 | 0.525 | 0.008 | 0.009 | 0.044 |
| 83 | 0.008 | 1.012 | 0.020 | 0.008 | 0.011 | 0.029 | 0.060 | 0.022 | 0.058 |
| 84 | 0.009 | 0.011 | 0.022 | 0.194 | 0.010 | 0.020 | 0.019 | 0.015 | 0.053 |
| 85 | 0.009 | 0.006 | 0.102 | 0.003 | 0.012 | 0.022 | 0.020 | 0.016 | 0.058 |
| 86 | 0.004 | 0.924 | 0.022 | 0.182 | 0.011 | 0.033 | 0.021 | 0.018 | 0.067 |

| | PROBE | | | | | |
|---|---|---|---|---|---|---|
| | 46 | 48 | 47 | 28 | | |
| | | OLIGO No. | | | | |
| DNA No. | 555-BSA | 867-BSA | 756-BSA | 862 | +control | TYPING |
| 71 | 0.583 | 0.016 | 0.009 | 0.039 | >2.500 | DRB1*11/DRB1*1301 |
| 72 | 0.012 | 0.010 | 0.009 | 0.013 | >2.500 | DRB1*0101/DRB5*0101 |
| 73 | 0.005 | 0.011 | 0.013 | 0.017 | >2.500 | DRB1*0101/DRB5*0101 |
| 75 | 0.011 | 0.007 | 0.010 | 0.045 | >2.500 | DRB1*0301/DRB1*04 |
| 78 | 0.005 | 0.005 | 0.006 | 0.062 | >2.500 | DRB1*0301/DRB1*07 |
| 79 | 0.790 | 0.013 | 0.009 | 0.122 | >2.500 | DRB1*0301/DRB1*1301 |
| 80 | 0.010 | 0.012 | 0.008 | 0.016 | >2.500 | DRB1*07/DRB5*0101 |
| 83 | 0.029 | 0.021 | 0.021 | 0.040 | >2.500 | DRB1*08/DRB5*0101 |
| 84 | 0.452 | 0.020 | 0.019 | 0.166 | >2.500 | DRB1*04/DRB1*1302 |
| 85 | 0.564 | 0.023 | 0.021 | 0.244 | >2.500 | DRB1*03/DRB1*13 |
| 86 | 0.017 | 0.017 | 0.020 | 0.038 | >2.500 | DRB1*04/DRB5*0201–0202 |

EXAMPLE 12

The preferred hybridization buffer, designated PEG buffer, used for HLA-DR typing as described in Example 8 has the following composition: 0.1M sodium phosphate, pH 7, 0.5M NaCl, 0.65% Tween 20, 0.14 mg/ml salmon sperm DNA (Sigma D 9156), 2% PEG 4000 (Merck 807490).

The same buffer containing formamide (10% final) has been used. Formamide is known to enable the hybridization temperature to be reduced.

If hybridization is still performed at 37° C. in the presence of formamide, the specificity of the detection should hence be increased.

Typing is carried out on 24 DNAs which are those which have been used in Example 10.

The capture probes used and the values obtained are given in Table 13 below.

TABLE 13

| | PROBE | | | | | | | | | | | |
|---|---|---|---|---|---|---|---|---|---|---|---|---|
| | 1 | 5 | 43 | 9 | 10 | 14 | 17 | 44 | 45 | 46 | 48 | 47 |
| | | | | | | OLIGO No. | | | | | | |
| DNA No. | 563 | 603 | 571-BSA | 545 | 398 | 591 | 595 | 574-BSA | 556-BSA | 555-BSA | 867-BSA | 756-BSA |
| 58 | 0.004 | 0.015 | 0.075 | 0.005 | 0.005 | 0.467 | 0.005 | 0.005 | 0.008 | 0.008 | 0.020 | 0.008 |
| 59 | 0.084 | 0.015 | 0.016 | 0.004 | 0.005 | 0.426 | 0.007 | 0.006 | 0.007 | 0.008 | 0.018 | 0.007 |
| 63 | 0.009 | 0.008 | 0.019 | 0.008 | 0.010 | 0.007 | 0.006 | 0.008 | 0.009 | 0.351 | 0.020 | 0.009 |
| 66 | 0.007 | 0.022 | 0.017 | 0.009 | 0.008 | 0.684 | 0.005 | 0.006 | 0.005 | 0.009 | 0.018 | 0.008 |
| 67 | 0.118 | 0.039 | 0.017 | 0.015 | 0.356 | 0.027 | 0.008 | 0.004 | 0.004 | 0.343 | 0.016 | 0.004 |
| 68 | 0.010 | 0.015 | 0.020 | 0.010 | 0.009 | 0.445 | 0.004 | 0.002 | 0.008 | 0.332 | 0.012 | 0.007 |
| 70 | 0.105 | 0.009 | 0.016 | 0.010 | 0.010 | 0.011 | 0.009 | 0.008 | 0.009 | 0.008 | 0.014 | 0.340 |
| 71 | 0.007 | 0.007 | 0.018 | 0.011 | 0.393 | 0.010 | 0.006 | 0.007 | 0.012 | 0.344 | 0.015 | 0.005 |
| 72 | 0.085 | 0.395 | 0.018 | 0.008 | 0.008 | 0.007 | 0.007 | 0.009 | 0.015 | 0.007 | 0.018 | 0.004 |
| 73 | 0.094 | 0.353 | 0.017 | 0.010 | 0.009 | 0.012 | 0.006 | 0.008 | 0.005 | 0.007 | 0.019 | 0.008 |
| 75 | 0.009 | 0.014 | 0.062 | 0.132 | 0.010 | 0.011 | 0.005 | 0.004 | 0.008 | 0.008 | 0.020 | 0.009 |
| 78 | 0.006 | 0.009 | 0.074 | 0.011 | 0.008 | 0.415 | 0.006 | 0.012 | 0.006 | 0.004 | 0.012 | 0.006 |
| 79 | 0.005 | 0.006 | 0.043 | 0.005 | 0.004 | 0.005 | 0.007 | 0.005 | 0.009 | 0.388 | 0.014 | 0.005 |
| 80 | 0.003 | 0.213 | 0.013 | 0.003 | 0.002 | 0.211 | 0.008 | 0.006 | 0.010 | 0.011 | 0.012 | 0.008 |
| 83 | 0.007 | 0.391 | 0.015 | 0.005 | 0.005 | 0.005 | 0.023 | 0.008 | 0.012 | 0.015 | 0.010 | 0.004 |

TABLE 13-continued

| | | | | | | | | | | | | |
|---|---|---|---|---|---|---|---|---|---|---|---|---|
| 84 | 0.004 | 0.008 | 0.013 | 0.110 | 0.005 | 0.007 | 0.003 | 0.006 | 0.005 | 0.410 | 0.018 | 0.002 |
| 85 | 0.007 | 0.007 | 0.033 | 0.007 | 0.006 | 0.006 | 0.006 | 0.003 | 0.008 | 0.371 | 0.018 | 0.005 |
| 86 | 0.009 | 0.203 | 0.020 | 0.081 | 0.007 | 0.005 | 0.005 | 0.005 | 0.009 | 0.048 | 0.016 | 0.005 |
| 87 | 0.008 | 0.289 | 0.015 | 0.009 | 0.008 | 0.008 | 0.006 | 0.004 | 0.004 | 0.323 | 0.014 | 0.006 |
| 89 | 0.008 | 0.010 | 0.015 | 0.091 | 0.002 | 0.004 | 0.007 | 0.005 | 0.012 | 0.009 | 0.013 | 0.007 |
| 90 | 0.033 | 0.007 | 0.015 | 0.075 | 0.003 | 0.009 | 0.007 | 0.004 | 0.001 | 0.008 | 0.014 | 0.008 |
| 91 | 0.077 | 0.006 | 0.013 | 0.006 | 0.005 | 0.006 | 0.009 | 0.006 | 0.013 | 0.009 | 0.015 | 0.002 |
| 92 | 0.042 | 0.009 | 0.013 | 0.009 | 0.006 | 0.007 | 0.008 | 0.009 | 0.005 | 0.012 | 0.017 | 0.003 |
| 95 | 0.005 | 0.004 | 0.015 | 0.006 | 0.006 | 0.006 | 0.008 | 0.002 | 0.008 | 0.319 | 0.308 | 0.005 |

| | PROBE | | | | | | | |
|---|---|---|---|---|---|---|---|---|
| | 28 | 24 | 27 | 52 | 37 | | | 42 |
| | | | | OLIGO No. | | | | |
| DNA No. | 802 | 1066 | 1068 | 997-BSA | 1033 | 1060 | +control | DNA No. TYPING |
| 58 | 0.036 | 0.005 | 0.001 | 0.004 | 0.207 | 0.009 | >2.500 | 58 DRB1*0301/DRB1*07 |
| 59 | 0.002 | 0.006 | 0.008 | 0.004 | 0.009 | 0.010 | >2.500 | 59 DRB1*0101–0102/DRB1*07 |
| 63 | 0.026 | 0.115 | 0.058 | 0.029 | 0.261 | 0.011 | >2.500 | 63 DRB1*12/DRB1*1301 |
| 66 | 0.007 | 0.005 | 0.007 | 0.008 | 0.012 | 0.010 | >2.500 | 66 DRB1*07/— |
| 67 | 0.009 | 0.005 | 0.008 | 0.009 | 0.251 | 0.024 | >2.500 | 67 DRB1*01/DRB1*11 |
| 68 | 0.036 | 0.006 | 0.009 | 0.010 | 0.016 | 0.011 | >2.500 | 68 DRB1*07/DRB1*1302 |
| 70 | 0.008 | 0.004 | 0.055 | 0.008 | 0.199 | 0.009 | >2.500 | 70 DRB1*1401/DRB1*0101–0102 |
| 71 | 0.034 | 0.003 | 0.005 | 0.009 | 0.539 | 0.008 | >2.500 | 71 DRB1*11/DRB1*1301 |
| 72 | 0.010 | 0.009 | 0.006 | 0.004 | 0.009 | 0.130 | >2.500 | 72 DRB1*0101/DRB5*0101 |
| 73 | 0.010 | 0.009 | 0.005 | 0.005 | 0.010 | 0.150 | >2.500 | 73 DRB1*0101/DRB5*0101 |
| 75 | 0.038 | 0.008 | 0.008 | 0.021 | 0.014 | 0.010 | >2.500 | 75 DRB1*0301/DRB1*04 |
| 78 | 0.041 | 0.007 | 0.004 | 0.007 | 0.254 | 0.015 | >2.500 | 78 DRB1*0301/DRB1*07 |
| 79 | 0.064 | 0.007 | 0.006 | 0.028 | 0.315 | 0.012 | >2.500 | 79 DRB1*0301/DRB1*1301 |
| 80 | 0.007 | 0.008 | 0.009 | 0.008 | 0.011 | 0.142 | >2.500 | 80 DRB1*07/DRB5*0101 |
| 83 | 0.010 | 0.166 | 0.007 | 0.009 | 0.017 | 0.159 | >2.500 | 83 DRB1*08/DRB5*0101 |
| 84 | 0.050 | 0.006 | 0.008 | 0.010 | 0.014 | 0.009 | >2.500 | 84 DRB1*04/DRB1*1302 |
| 85 | 0.063 | 0.009 | 0.007 | 0.036 | 0.009 | 0.011 | >2.500 | 85 DRB1*03/DRB1*13 |
| 86 | 0.014 | 0.008 | 0.004 | 0.011 | 0.010 | 0.010 | >2.500 | 86 DRB1*04/DRB5*0201–0202 |
| 87 | 0.042 | 0.007 | 0.005 | 0.028 | 0.007 | 0.004 | >2.500 | 87 DRB1*1301/DRB5*0201–0202 |
| 89 | 0.008 | 0.068 | 0.039 | 0.005 | 0.201 | 0.006 | >2.500 | 89 DRB1*04/DRB1*12 |
| 90 | 0.008 | 0.011 | 0.009 | 0.006 | 0.010 | 0.009 | >2.500 | 90 DRB1*0101/DRB1*04 |
| 91 | 0.010 | 9.010 | 0.006 | 0.008 | 0.009 | 0.011 | >2.500 | 91 DRB1*0101/ |
| 92 | 0.040 | 0.007 | 0.012 | 0.028 | 0.018 | 0.012 | >2.500 | 92 DRB1*0101/DRB1*1402 |
| 95 | 0.035 | 0.008 | 0.009 | 0.030 | 0.017 | 0.009 | >2.500 | 95 DRB1*1302/DRB1*1303 |

The preferred hybridization temperature is 37° C. and the preferred hybridization buffer is PEG buffer but, as the results of Examples 11 and 12 show, it is seen to be possible to vary both the hybridization temperature and the hybridization buffer.

As is apparent from the foregoing description, the method of the present invention combines the following practical advantages; an optimal specificity with possible discrimination of all the alleles, a simplicity of implementation and a reduced cost relative to serological analysis, a rapid implementation with results obtained approximately 90 minutes after amplification, equivalent to a total time period of less than 12 hours, which is essential for kidney donors, a compatibility with individual typing, which is essential for emergency typings and use in small laboratories, a signal which is quantifiable by measurement of optical density and processing of the results, where appropriate, using a simple computerized system, and an adaptability to automatic systems.

---

We claim:

1. A nucleotide probe having a nucleotide sequence selected from the group consisting of: SEQ ID NOs: 78–81 and their complementary sequences.

2. A set of nucleotide probes for determining HLA-DR types or sub-types, comprising at least one first probe having a nucleotide sequence selected from the group consisting of: SEQ ID NOs: 78–81 and their complementary sequences.

3. The set of probes as claimed in claim 2, further comprising at least one second probe having a nucleotide sequence selected from the group consisting of:

(G)TGGACAACTACT(G) (SEQ ID NO: 3),
GATACTTCTATCACC(AA) (SEQ ID NO: 4),
(G)CCTGATGAGGAGTA(C) (SEQ ID NO: 5),
(T)GGCAGGGTAAGTATAAG (SEQ ID NO: 6),
(G)GGCCCTGGTGGA(CA) (SEQ ID NO: 7),
(T)GCGGTATCTGCACA (SEQ ID NO: 8),
GGAGGAGGTTAAG(TT) (SEQ ID NO: 9),
(C)TGGAAGACGAGC(G) (SEQ ID NO: 10),
(T)GGAAGACAAGCG(G) (SEQ ID NO: 11),
(T)GCGGAGCACTGG(A) (SEQ ID NO: 12),
(A)CCAGGAGGAGAACGT(G) (SEQ ID NO: 14),
(A)CTCTACGGGTGAGT(G) (SEQ ID NO: 15),
(G)ACACCTATTGCAGA(C) (SEQ ID NO: 16)

and their complementary sequences, wherein the nucleotides in parentheses are optional.

4. The set of probes as claimed in claim 3, wherein said at least one second probe has a sequence of the non-parenthesized portion of a nucleotide sequence selected from the group consisting of:

(G)TGGACAACTACT(G) (SEQ ID NO: 3),
GATACTTCTATCACC(AA) (SEQ ID NO: 4),
(G)CCTGATGAGGAGTA(C) (SEQ ID NO: 5),
(T)GGCAGGGTAAGTATAAG (SEQ ID NO: 6), (G)GGCCCTGGTGGA(CA) (SEQ ID NO: 7),
(T)GCGGTATCTGCACA (SEQ ID NO: 8),
(C)TGGAAGACGAGC(G) (SEQ ID NO: 10),
(T)GGAAGACAAGCG(G) (SEQ ID NO: 11),
(T)GCGGAGCACTGG(A) (SEQ ID NO: 12),
(A)CTCTACGGGTGAGT(G) (SEQ ID NO: 15),
(G)ACACCTATTGCAGA(C) (SEQ ID NO: 16)
and their complementary sequences.

5. The set of probes as claimed in claim 2, further comprising a probe having a nucleotide sequence of GGAGGAGGTTAAGTT (SEQ ID NO: 9), or its complementary sequence.

6. The set of probes as claimed in claim 2, further comprising a probe having a nucleotide sequence of SEQ ID NO: 17, or its complementary sequence.

7. The set of probes as claimed in claim 2, further comprising at least one second probe having a nucleotide sequence selected from the group consisting of:
(G)AGGAGGACTTGCGC(T) (SEQ ID NO: 18),
(T)ACGGGGCTGTGGA(G) (SEQ ID NO: 19),
(G)GAGCTGCGTAAG(T) (SEQ ID NO: 20),
TTCCTGGAGAGACAC (SEQ ID NO: 21),
(G)GGAGAGATACTTC(C) (SEQ ID NO: 22)
and their complementary sequences, wherein the nucleotides in parentheses are optional.

8. The set of probes as claimed in claim 7, wherein said at least one second probe has a sequence of the non-parenthesized portion of a nucleotide sequence selected from the group consisting of:
(G)AGGAGGACTTGCGC(T) (SEQ ID NO: 18),
(T)ACGGGGCTGTGGA(G) (SEQ ID NO: 19),
(G)GAGCTGCGTAAG(T) (SEQ ID NO: 20),
TTCCTGGAGAGACAC (SEQ ID NO: 21),
(G)GGAGAGATACTTC(C) (SEQ ID NO: 22)
and their complementary sequences.

9. The set of probes as claimed in claim 2, further comprising at least one probe having a nucleotide sequence selected from the group consisting of: SEQ ID NO: 71, SEQ ID NO: 72, and their complementary sequences.

10. A method for determining the HLA-DR typing of an individual, comprising using the set of probes as defined in claim 2 as capture or detection probes.

11. The method as claimed in claim 10, wherein said set of probes further comprises at least one second probe having a nucleotide sequence selected from the group consisting of:
(G)TGGACAACTACT(G) (SEQ ID NO: 3),
GATACTTCTATCACC(AA) (SEQ ID NO: 4),
(G)CCTGATGAGGAGTA(C) (SEQ ID NO: 5),
(T)GGCAGGGTAAGTATAAG (SEQ ID NO: 6),
(G)GGCCCTGGTGGA(CA) (SEQ ID NO: 7),
(T)GCGGTATCTGCACA (SEQ ID NO: 8),
GGAGGAGGTTAAG(TT) (SEQ ID NO: 9),
(C)TGGAAGACGAGC(G) (SEQ ID NO: 10),
(T)GGAAGACAAGCG(G) (SEQ ID NO: 11),
(T)GCGGAGCACTGG(A) (SEQ ID NO: 12),
(A)CCAGGAGGAGAACGT(G) (SEQ ID NO: 14),
(A)CTCTACGGGTGAGT(G) (SEQ ID NO: 15),
(G)ACACCTATTGCAGA(C) (SEQ ID NO: 16)
(G)AGGAGGACTTGCGC(T) (SEQ ID NO: 18),
(T)ACGGGGCTGTGGA(G) (SEQ ID NO: 19),
(G)GAGCTGCGTAAG(T) (SEQ ID NO: 20),
TTCCTGGAGAGACAC (SEQ ID NO: 21),
(G)GGAGAGATACTTC(C) (SEQ ID NO: 22),
CCGGGCGGTGACIGAGCTGGGGC (SEQ ID NO: 71),
GAACAGCCAGAAGGAC (SEQ ID NO: 72)
and their complementary sequences, wherein the nucleotides in parentheses are optional.

12. The method as claimed in claim 10, wherein said set of probes further comprises at least one second probe having a nucleotide sequence selected from the group consisting of:
(G)TGGACAACTACT(G) (SEQ ID NO: 3),
GATACTTCTATCACC(AA) (SEQ ID NO: 4),
(G)CCTGATGAGGAGTA(C) (SEQ ID NO: 5),
(T)GGCAGGGTAAGTATAAG (SEQ ID NO: 6),
(G)GGCCCTGGTGGA(CA) (SEQ ID NO: 7),
(T)GCGGTATCTGCACA (SEQ ID NO: 8),
GGAGGAGGTTAAG(TT) (SEQ ID NO: 9),
(C)TGGAAGACGAGC(G) (SEQ ID NO: 10),
(T)GGAAGACAAGCG(G) (SEQ ID NO: 11),
(T)GCGGAGCACTGG(A) (SEQ ID NO: 12),
(A)CCAGGAGGAGAACGT(G) (SEQ ID NO: 14),
(A)CTCTACGGGTGAGT(G) (SEQ ID NO: 15),
(G)ACACCTATTGCAGA(C) (SEQ ID NO: 16)
AACCAGIAGGAGAACGT (SEQ ID NO: 17),
(G)AGGAGGACTTGCGC(T) (SEQ ID NO: 18),
(T)ACGGGGCTGTGGA(G) (SEQ ID NO: 19),
(G)GAGCTGCGTAAG(T) (SEQ ID NO: 20),
TTCCTGGAGAGACAC (SEQ ID NO: 21),
(G)GGAGAGATACTTC(C) (SEQ ID NO: 22)
and their complementary sequences, wherein the nucleotides in parentheses are optional.

13. The method as claimed in claim 10, wherein said set of probes further comprises at least one probe having a sequence of the non-parenthesized portion of a nucleotide sequence selected from the group consisting of:
(G)TGGACAACTACT(G) (SEQ ID NO: 3),
GATACTTCTATCACC(AA) (SEQ ID NO: 4),
(G)CCTGATCAGGAGTA(C) (SEQ ID NO: 5),
(T)GGCAGGGTAAGTATAAG (SEQ ID NO: 6),
(G)GGCCCTGGTGGA(CA) (SEQ ID NO: 7),
(T)GCGGTATCTGCACA (SEQ ID NO: 8),
GGAGGAGGTTAAGTT (SEQ ID NO: 9),
(C)TGGAAGACGAGC(G) (SEQ ID NO: 10),
(T)GGAAGACAAGCG(G) (SEQ ID NO: 11),
(T)GCGGAGCACTGG(A) (SEQ ID NO: 12),
(A)CTCTACGGGTGAGT(G) (SEQ ID NO: 15),
(G)ACACCTATTGCAGA(C) (SEQ ID NO: 16)
AACCAGIAGGAGAACGT (SEQ ID NO: 17),
(G)AGGAGGACTTGCGC(T) (SEQ ID NO: 18),
(T)ACGGGGCTGTGGA(G) (SEQ ID NO: 19),
(G)GAGCTGCGTAAG(T) (SEQ ID NO: 20),
TTCCTGGAGAGACAC (SEQ ID NO: 21),
(G)GGAGAGATACTTC(C) (SEQ ID NO: 22)
and their complementary sequences.

14. The method as claimed in claim 12, wherein said probes are used as capture probes.

15. The method as claimed in claim 14, said method comprising:
(a) immobilizing each capture probe on a solid support, (b) bringing each immobilized capture probe into contact with a liquid medium containing at least one target nucleic acid fragment under conditions permitting hybridization if a sequence complementary to the probe is present in the target, and (c) detecting any hybrids formed.

16. The method as claimed in claim 15, wherein each said immobilized capture probe is brought into contact with said liquid medium at a temperature of 37° C.

17. The set of probes as claimed in claim 2, wherein said probes are coupled with a ligand that facilitates binding to a solid support.

18. The set of probes as claimed in claim 17, wherein said ligand comprises at least one polar functional group.

19. The set of probes as claimed in claim 18, wherein said polar functional group is an amino group.

20. The set of probes as claimed in claim 17, wherein said ligand comprises a hydrophobic portion.

21. The set of probes as claimed in claim 2, wherein said probes are coupled with a ligand comprising a group of formula (I)

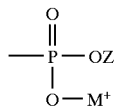

(I)

wherein Z represents a linear or branched alkyl or alkenyl radical having 2 to 12 carbon atoms, unsubstituted or substituted with one or more hydroxyl or amino groups, and M+ represents an alkali metal or ammonium cation.

22. The set of probes as claimed in claim 2, wherein said probes are coupled with a ligand comprising a group of formula (II)

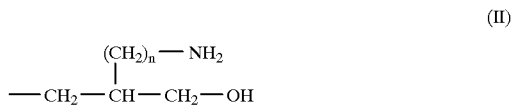

(II)

in which n is an integer from 1 to 4.

23. The set of probes as claimed in claim 2, wherein said probes are coupled with a ligand comprising a peptide or a protein.

24. The set of probes as claimed in claim 23, wherein said protein is an albumin.

25. The set of probes as claimed in claim 24, wherein said albumin is bovine serum albumin.

26. The set of probes as claimed in claim 2, wherein said probes are adsorbed to a solid support.

27. The set of probes as claimed in claim 17, wherein said probes are adsorbed to a solid support.

* * * * *

SEQUENCE LISTING (1) GENERAL INFORMATION:

(iii) NUMBER OF SEQUENCES: 81

(2) INFORMATION FOR SEQ ID NO:1:

(i) SEQUENCE CHARACTERISTICS:
      (A) LENGTH: 15 base pairs
      (B) TYPE: nucleic acid
      (C) STRANDEDNESS: single
      (D) TOPOLOGY: linear (xi) SEQUENCE DESCRIPTION: SEQ ID NO:1:

GCTGGAAAGA TGCAT                                                              15

(2) INFORMATION FOR SEQ ID NO:2:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:2:

CAGCAGGATA AGTATGA                                                            17

(2) INFORMATION FOR SEQ ID NO:3:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO:3:

GTGGACAACT ACTG                                                               14

(2) INFORMATION FOR SEQ ID NO:4:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:4:

GATACTTCTA TCACCAA                                                            17

(2) INFORMATION FOR SEQ ID NO:5:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:5:

GCCTGATGAG GAGTAC                                                             16

(2) INFORMATION FOR SEQ ID NO:6:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:6:

TGGCAGGGTA AGTATAAG                                                           18

(2) INFORMATION FOR SEQ ID NO:7:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:7:

GGGCCCTGGT GGACA                                                              15

(2) INFORMATION FOR SEQ ID NO:8:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:8:

TGCGGTATCT GCACA                                                      15

(2) INFORMATION FOR SEQ ID NO:9:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:9:

GGAGGAGGTT AAGTT                                                      15

(2) INFORMATION FOR SEQ ID NO:10:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO:10:

CTGGAAGACG AGCG                                                      14

(2) INFORMATION FOR SEQ ID NO:11:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO:11:

TGGAAGACAA GCGG                                                      14

(2) INFORMATION FOR SEQ ID NO:12:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO:12:

TGCGGAGCAC TGGA                                                      14

(2) INFORMATION FOR SEQ ID NO:13:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ix) FEATURE:
        (A) NAME/KEY: modified_base
        (B) LOCATION: 6
        (D) OTHER INFORMATION: /mod_base= i
                              /label= N (xi) SEQUENCE DESCRIPTION: SEQ ID NO:13:

ACCAGNAGGA GAACGTG                                                         17

(2) INFORMATION FOR SEQ ID NO:14:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:14:

ACCAGGAGGA GAACGTG                                                         17

(2) INFORMATION FOR SEQ ID NO:15:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:15:

ACTCTACGGG TGAGTG                                                          16

(2) INFORMATION FOR SEQ ID NO:16:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:16:

GACACCTATT GCAGAC                                                          16

(2) INFORMATION FOR SEQ ID NO:17:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ix) FEATURE:
        (A) NAME/KEY: modified_base
        (B) LOCATION: 7
        (D) OTHER INFORMATION: /mod_base= i
                               /label= N (xi) SEQUENCE DESCRIPTION: SEQ ID NO:17:

AACCAGNAGG AGAACGT                                                         17

(2) INFORMATION FOR SEQ ID NO:18:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:18:

GAGGAGGACT TGCGCT                                                          16

(2) INFORMATION FOR SEQ ID NO:19:

(i) SEQUENCE CHARACTERISTICS:

(A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:19:

TACGGGGCTG TGGAG                                                              15

(2) INFORMATION FOR SEQ ID NO:20:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO:20:

GGAGCTGCGT AAGT                                                               14

(2) INFORMATION FOR SEQ ID NO:21:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:21:

TTCCTGGAGA GACAC                                                              15

(2) INFORMATION FOR SEQ ID NO:22:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:22:

GGGAGAGATA CTTCC                                                              15

(2) INFORMATION FOR SEQ ID NO:23:

(i) SEQUENCE CHARACTERISTICS:
        (A) LENGTH: 90 amino acids
        (B) TYPE: amino acid
        (C) STRANDEDNESS: single
        (D) TOPOLOGY: linear (xi) SEQUENCE DESCRIPTION: SEQ ID NO:23:

Pro Arg Phe Leu Glu Gln Xaa Lys Ser Glu Cys His Phe Phe Asn Gly
    1               5                  10                  15

Thr Glu Arg Val Arg Phe Leu Asp Arg Tyr Phe Tyr Asn Gln Glu Glu
                20                  25                  30

Tyr Val Arg Phe Asp Ser Asp Val Gly Glu Tyr Arg Ala Val Thr Glu
                35                  40                  45

Leu Gly Arg Pro Asp Ala Glu Tyr Trp Asn Ser Gln Lys Asp Leu Leu
            50                  55                  60

Glu Gln Arg Arg Ala Ala Val Asp Thr Tyr Cys Arg His Asn Tyr Gly
    65                  70                  75                  80

Val Gly Glu Ser Phe Thr Val Gln Arg Arg
                    85                  90

(2) INFORMATION FOR SEQ ID NO:24:

(i) SEQUENCE CHARACTERISTICS:
        (A) LENGTH: 269 base pairs
        (B) TYPE: nucleic acid
        (C) STRANDEDNESS: single
        (D) TOPOLOGY: linear (xi) SEQUENCE DESCRIPTION: SEQ ID NO:24:

```
CACGTTTCTT GGAGCAGNNT AAGTCTGAGT GTCATTTCTT CAATGGGACG GAGCGGGTGC      60

GGTTCCTGGA CAGATACTTC TATAACCAGG AGGAGTACGT GCGCTTCGAC AGCGACGTGG     120

GGGAGTACCG GGCGGTGACG GAGCTGGGGC GGCCTGATGC CGAGTACTGG AACAGCCAGA     180

AGGACCTCCT GGAGCAGANG CGGGCCGNGG TGGACACCTA CTGCAGACAC AACTACGGGG     240

TTGGTGAGAG CTTCACAGTG CAGCGGCGA                                       269
```

(2) INFORMATION FOR SEQ ID NO:25:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (xi) SEQUENCE DESCRIPTION: SEQ ID NO:25:

```
CTGGAAAGAT GCA                                                         13
```

(2) INFORMATION FOR SEQ ID NO:26:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (xi) SEQUENCE DESCRIPTION: SEQ ID NO:26:

```
TGGAAAGATG CAT                                                         13
```

(2) INFORMATION FOR SEQ ID NO:27:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO:27:

```
CAGGATAAGT ATGA                                                        14
```

(2) INFORMATION FOR SEQ ID NO:28:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:28:

```
GCAGGATAAG TATGA                                                       15
```

(2) INFORMATION FOR SEQ ID NO:29:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:29:

CAGCAGGATA AGTATG 16

(2) INFORMATION FOR SEQ ID NO:30:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (xi) SEQUENCE DESCRIPTION: SEQ ID NO:30:

TGGACAACTA CTG 13

(2) INFORMATION FOR SEQ ID NO:31:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (xi) SEQUENCE DESCRIPTION: SEQ ID NO:31:

GGACAACTAC TG 12

(2) INFORMATION FOR SEQ ID NO:32:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:32:

GATACTTCTA TCACC 15

(2) INFORMATION FOR SEQ ID NO:33:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO:33:

CCTGATGAGG AGTA 14

(2) INFORMATION FOR SEQ ID NO:34:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:34:

CAGGGTAAGT ATAAG 15

(2) INFORMATION FOR SEQ ID NO:35:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:35:

GCAGGGTAAG TATAAG 16

(2) INFORMATION FOR SEQ ID NO:36:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:36:

TGGCAGGGTA AGTAT                                  15

(2) INFORMATION FOR SEQ ID NO:37:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:37:

GGCAGGGTAA GTATAAG                              17

(2) INFORMATION FOR SEQ ID NO:38:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (xi) SEQUENCE DESCRIPTION: SEQ ID NO:38:

GGCCCTGGTG GA                                        12

(2) INFORMATION FOR SEQ ID NO:39:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO:39:

GCGGTATCTG CACA                                  14

(2) INFORMATION FOR SEQ ID NO:40:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (xi) SEQUENCE DESCRIPTION: SEQ ID NO:40:

GGAGGAGGTT AAG                                   13

(2) INFORMATION FOR SEQ ID NO:41:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (xi) SEQUENCE DESCRIPTION: SEQ ID NO:41:

TGGAAGACGA GC                                        12

(2) INFORMATION FOR SEQ ID NO:42:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (xi) SEQUENCE DESCRIPTION: SEQ ID NO:42:

GGAAGACAAG CG                                                                         12

(2) INFORMATION FOR SEQ ID NO:43:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (xi) SEQUENCE DESCRIPTION: SEQ ID NO:43:

CTCTACGGGT GAG                                                                     13

(2) INFORMATION FOR SEQ ID NO:44:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO:44:

CTCTACGGGT GAGT                                                               14

(2) INFORMATION FOR SEQ ID NO:45:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (xi) SEQUENCE DESCRIPTION: SEQ ID NO:45:

CACCTATTGC AGA                                                                    13

(2) INFORMATION FOR SEQ ID NO:46:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO:46:

CACCTATTGC AGAC                                                               14

(2) INFORMATION FOR SEQ ID NO:47:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO:47:

ACACCTATTG CAGA                                                              14

(2) INFORMATION FOR SEQ ID NO:48:

```
    (i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:48:

CCAGGAGGAG AACGT                                                     15

(2) INFORMATION FOR SEQ ID NO:49:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ix) FEATURE:
        (A) NAME/KEY: modified_base
        (B) LOCATION: 5
        (D) OTHER INFORMATION: /mod_base= i
                               /label= N (xi) SEQUENCE DESCRIPTION: SEQ ID NO:49:

CCAGNAGGAG AACGT                                                     15

(2) INFORMATION FOR SEQ ID NO:50:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ix) FEATURE:
        (A) NAME/KEY: modified_base
        (B) LOCATION: 6
        (D) OTHER INFORMATION: /mod_base= i
                               /label= N (xi) SEQUENCE DESCRIPTION: SEQ ID NO:50:

ACCAGNAGGA GAACGT                                                    16

(2) INFORMATION FOR SEQ ID NO:51:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (xi) SEQUENCE DESCRIPTION: SEQ ID NO:51:

GAGCTGCGTA AG                                                        12

(2) INFORMATION FOR SEQ ID NO:52:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:52:

TTCCTGGAGA GATAC                                                     15

(2) INFORMATION FOR SEQ ID NO:53:

(i) SEQUENCE CHARACTERISTICS:
        (A) LENGTH: 15 base pairs
        (B) TYPE: nucleic acid
```

```
            (C) STRANDEDNESS: single
            (D) TOPOLOGY: linear (xi) SEQUENCE DESCRIPTION: SEQ ID NO:53:

TCCTGGAGAG ATACT                                                           15

(2) INFORMATION FOR SEQ ID NO:54:

(i) SEQUENCE CHARACTERISTICS:
            (A) LENGTH: 13 base pairs
            (B) TYPE: nucleic acid
            (C) STRANDEDNESS: single
            (D) TOPOLOGY: linear (xi) SEQUENCE DESCRIPTION: SEQ ID NO:54:

GGAGGACTTG CGC                                                             13

(2) INFORMATION FOR SEQ ID NO:55:

(i) SEQUENCE CHARACTERISTICS:
            (A) LENGTH: 14 base pairs
            (B) TYPE: nucleic acid
            (C) STRANDEDNESS: single
            (D) TOPOLOGY: linear (xi) SEQUENCE DESCRIPTION: SEQ ID NO:55:

GGAGGACTTG CGCT                                                            14

(2) INFORMATION FOR SEQ ID NO:56:

(i) SEQUENCE CHARACTERISTICS:
            (A) LENGTH: 14 base pairs
            (B) TYPE: nucleic acid
            (C) STRANDEDNESS: single
            (D) TOPOLOGY: linear (xi) SEQUENCE DESCRIPTION: SEQ ID NO:56:

AGGAGGACTT GCGC                                                            14

(2) INFORMATION FOR SEQ ID NO:57:

(i) SEQUENCE CHARACTERISTICS:
            (A) LENGTH: 13 base pairs
            (B) TYPE: nucleic acid
            (C) STRANDEDNESS: single
            (D) TOPOLOGY: linear (xi) SEQUENCE DESCRIPTION: SEQ ID NO:57:

ACGGGGCTGT GGA                                                             13

(2) INFORMATION FOR SEQ ID NO:58:

(i) SEQUENCE CHARACTERISTICS:
            (A) LENGTH: 12 base pairs
            (B) TYPE: nucleic acid
            (C) STRANDEDNESS: single
            (D) TOPOLOGY: linear (xi) SEQUENCE DESCRIPTION: SEQ ID NO:58:

TGGACAACTA CT                                                              12

(2) INFORMATION FOR SEQ ID NO:59:

(i) SEQUENCE CHARACTERISTICS:
            (A) LENGTH: 12 base pairs
            (B) TYPE: nucleic acid
            (C) STRANDEDNESS: single
            (D) TOPOLOGY: linear
```

(xi) SEQUENCE DESCRIPTION: SEQ ID NO:59:

GCGGAGCACT GG                                                      12

(2) INFORMATION FOR SEQ ID NO:60:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (xi) SEQUENCE DESCRIPTION: SEQ ID NO:60:

TGGAAGACAA GC                                                      12

(2) INFORMATION FOR SEQ ID NO:61:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:61:

GAGGAGCTCC TGCGCT                                                  16

(2) INFORMATION FOR SEQ ID NO:62:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (xi) SEQUENCE DESCRIPTION: SEQ ID NO:62:

AGGAGAACGT GC                                                      12

(2) INFORMATION FOR SEQ ID NO:63:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (xi) SEQUENCE DESCRIPTION: SEQ ID NO:63:

AGCTGCGTAA GT                                                      12

(2) INFORMATION FOR SEQ ID NO:64:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (xi) SEQUENCE DESCRIPTION: SEQ ID NO:64:

GAGAGACACT TCC                                                     13

(2) INFORMATION FOR SEQ ID NO:65:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (xi) SEQUENCE DESCRIPTION: SEQ ID NO:65:

GGAGAGATAC TTC                           13

(2) INFORMATION FOR SEQ ID NO:66:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (xi) SEQUENCE DESCRIPTION: SEQ ID NO:66:

GAGAGATACT TCC                           13

(2) INFORMATION FOR SEQ ID NO:67:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (xi) SEQUENCE DESCRIPTION: SEQ ID NO:67:

ACGGGGCTGT G                             11

(2) INFORMATION FOR SEQ ID NO:68:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (xi) SEQUENCE DESCRIPTION: SEQ ID NO:68:

TACGGGGCTG T                             11

(2) INFORMATION FOR SEQ ID NO:69:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (xi) SEQUENCE DESCRIPTION: SEQ ID NO:69:

CGGGGCTGTG G                             11

(2) INFORMATION FOR SEQ ID NO:70:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:70:

CCGGGCGGTG ACGTGAGCTG GGGC                24

(2) INFORMATION FOR SEQ ID NO:71:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ix) FEATURE:
        (A) NAME/KEY: modified_base
        (B) LOCATION: 13

(D) OTHER INFORMATION: /mod_base= i
                                  /label= N (xi) SEQUENCE DESCRIPTION: SEQ ID NO:71:

CCGGGCGGTG ACNGAGCTGG GGC                                                  23

(2) INFORMATION FOR SEQ ID NO:72:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:72:

GAACAGCCAG AAGGAC                                                          16

(2) INFORMATION FOR SEQ ID NO:73:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:73:

CCGGATCCTT CGTGTCCCCA CAGCACG                                              27

(2) INFORMATION FOR SEQ ID NO:74:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:74:

TCGCCGCTGC ACTGTGAAG                                                       19

(2) INFORMATION FOR SEQ ID NO:75:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:75:

GGGGAGTACC GGGCGGTGAC GGAGCTGGGG CGGCCT                                    36

(2) INFORMATION FOR SEQ ID NO:76:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:76:

CCGGGCGGTG ACGGAGCTGG GGC                                                  23

(2) INFORMATION FOR SEQ ID NO:77:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:77:

CCGGGCGGTG ACTGAGCTGG GGC                                        23

(2) INFORMATION FOR SEQ ID NO:78:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:78:

TGGCAGCTTA AGTTT                                                 15

(2) INFORMATION FOR SEQ ID NO:79:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO:79:

CCTAAGAGGG AGTG                                                  14

(2) INFORMATION FOR SEQ ID NO:80:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:80:

GCGAGTGTGG AACCT                                                 15

(2) INFORMATION FOR SEQ ID NO:81:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (xi) SEQUENCE DESCRIPTION: SEQ ID NO:81:

AAGACAGGCG GGC                                                   13